(12) United States Patent
Yamaguchi et al.

(10) Patent No.: US 11,607,123 B2
(45) Date of Patent: Mar. 21, 2023

(54) OPHTHALMOLOGIC APPARATUS

(71) Applicant: TOPCON CORPORATION, Tokyo (JP)

(72) Inventors: Tatsuo Yamaguchi, Warabi (JP); Michiko Nakanishi, Tokyo (JP); Taichi Yuasa, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 555 days.

(21) Appl. No.: 16/732,410

(22) Filed: Jan. 2, 2020

(65) Prior Publication Data

US 2020/0138283 A1 May 7, 2020

Related U.S. Application Data

(63) Continuation of application No. PCT/JP2018/021307, filed on Jun. 4, 2018.

(30) Foreign Application Priority Data

Jul. 5, 2017 (JP) .............................. JP2017-131593

(51) Int. Cl.
*A61B 3/00* (2006.01)
*A61B 3/10* (2006.01)

(52) U.S. Cl.
CPC .......... *A61B 3/0083* (2013.01); *A61B 3/0025* (2013.01); *A61B 3/0091* (2013.01); *A61B 3/102* (2013.01)

(58) Field of Classification Search
CPC ... A61B 3/0083; A61B 3/0025; A61B 3/0091; A61B 3/102

USPC ........................................................ 600/425
See application file for complete search history.

(56) References Cited

U.S. PATENT DOCUMENTS

| 5,815,242 | A | 9/1998 | Anderson et al. |
| 10,772,497 | B2 * | 9/2020 | Walsh .................... A61B 3/15 |
| 11,039,741 | B2 * | 6/2021 | Walsh .................... A61B 3/10 |
| 2003/0103191 | A1 | 6/2003 | Staurenghi et al. |

(Continued)

FOREIGN PATENT DOCUMENTS

| EP | 1308124 A2 | 5/2003 |
| JP | 2000-041943 A | 2/2000 |

(Continued)

OTHER PUBLICATIONS

International Search Report and Written Opinion dated Aug. 14, 2018, in connection with International Patent Application Serial No. PCT/JP2018/021307, 11 pgs.

*Primary Examiner* — Collin X Beatty
(74) *Attorney, Agent, or Firm* — Chiesa Shahinian & Giantomasi PC

(57) ABSTRACT

An ophthalmologic apparatus includes: an optical system configured to acquire data of a subject's eye; a housing unit configured to house the optical system; and an attachment member including a holding member configured to hold a face of the subject movably in a state where a peripheral site of the subject's eye is in contact with the holding member, a passing part through which an optical axis of the optical system passes being formed in the holding member, and the attachment member configured to be detachable between the housing unit and the subject's eye.

12 Claims, 14 Drawing Sheets

(56) References Cited

U.S. PATENT DOCUMENTS

2011/0099718 A1  5/2011  Eilers et al.
2013/0194094 A1  8/2013  Nakahara et al.

FOREIGN PATENT DOCUMENTS

JP  2000-041946 A  2/2000
JP  2013-153796 A  8/2013

* cited by examiner

OPHTHALMOLOGIC APPARATUS

CROSS-REFERENCE TO RELATED APPLICATIONS

The present application is a continuation application of International Patent Application Serial No. PCT/JP2018/021307, filed Jun. 4, 2018, which claims priority to Japanese Patent Application Serial No. 2017-131593, filed Jul. 5, 2017. The contents of these applications are incorporated herein by reference in their entirety.

TECHNICAL FIELD

The disclosure relates to an ophthalmologic apparatus.

BACKGROUND

There is a demand for ophthalmologic apparatuses capable of easily observing and imaging fundus of a subject's eye with a wide field of view for screening or treating eye diseases. Optical coherence tomography and Scanning Laser Ophthalmoscope (hereinafter, SLO) are known as such ophthalmologic apparatuses. The SLO is an apparatus configured to form an image of the fundus by scanning the fundus with light to detect returning light of the light with a light receiving device.

In general, in order to observe the fundus and the like with a wide field of view using ophthalmologic apparatuses, the diameter of the objective lens needs to be increased. However, increasing the diameter of the objective lens leads to increase the cost and the size of the apparatus. Therefore, various methods of observing the fundus and the like with a wide field of view while suppressing the increase of the diameter of the objective lens have been proposed.

For example, in European Patent Application Publication No. 1308124, a technique of acquiring a wide-angle image of the subject's eye, by bringing a contact lens included in an objective lens system into contact with a cornea of the subject's eye, is disclosed. For example, in U.S. Pat. No. 5,815,242, a technique of providing an anterior segment imaging system and imaging an anterior segment of the subject's eye with the anterior segment imaging system, in an ophthalmologic apparatus for acquiring a wide-angle image of the subject's eye using an ellipsoidal mirror, is disclosed.

SUMMARY

One aspect of embodiments is an ophthalmologic apparatus, including: an optical system configured to acquire data of a subject's eye; a housing unit configured to house the optical system; and an attachment member including a holding member configured to hold a face of the subject movably in a state where a peripheral site of the subject's eye is in contact with the holding member, a passing part through which an optical axis of the optical system passes being formed in the holding member, and the attachment member configured to be detachable between the housing unit and the subject's eye.

DETAILED DESCRIPTION

Figure 1:
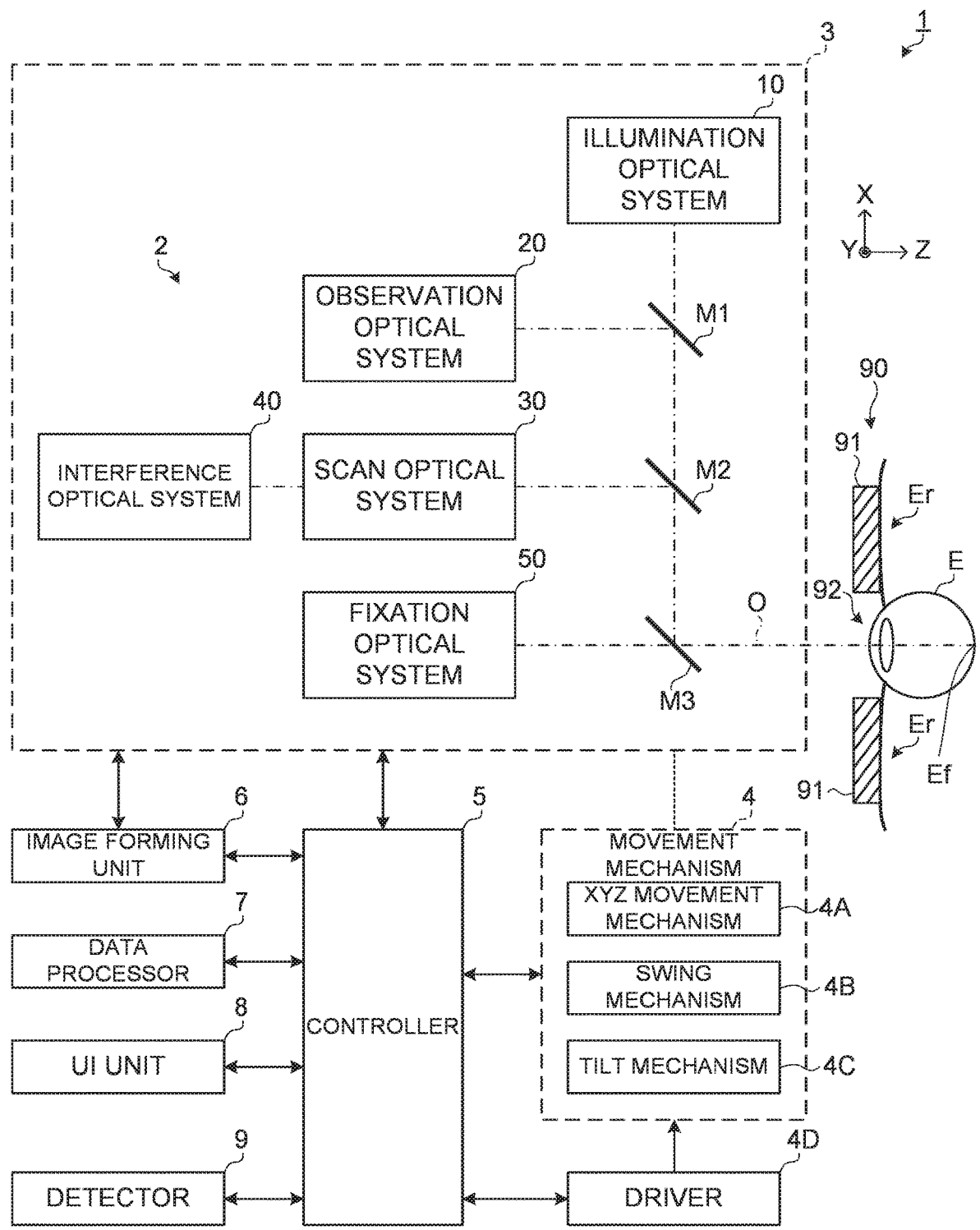
FIG. 1 is a schematic diagram illustrating an example of the configuration of an ophthalmologic apparatus according to embodiments.

In the ophthalmologic apparatus for acquiring the image of the subject's eye with a wide field of view known to the inventors of the present application, the working distance, which is a distance between the subject's eye and the optical system of apparatus (objective lens), is short. Therefore, depending on the shape of the subject's face, the possibility that the apparatus (body, optical system) contacts the subject (a part of the face, subject's eye) increases by the alignment operation of the subject or the auto alignment operation.

According to some embodiments of the present invention, unintended contact between the subject and the apparatus can be avoided even in an ophthalmologic apparatus having a short working distance.

Referring now to the drawings, exemplary embodiments of an ophthalmologic apparatus according to the present invention are described below. In the embodiments, any of the techniques disclosed in the documents cited in the present specification can be applied to the embodiments below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The ophthalmologic apparatus according to the embodiments can scan a posterior segment of a subject's eye with light beam to acquire a distribution of predetermined data (for example, an image, a layer thickness distribution, a lesion distribution). Examples of such the ophthalmologic apparatus include optical coherence tomography, SLO, and the like.

The ophthalmologic apparatus according to the embodiments may be provided a function of projecting a fixation target onto a fundus of the subject's eye. An internal fixation target or an external fixation target can be used as the fixation target.

In the following description, unless otherwise stated, the left-right direction (horizontal direction) viewed from the subject is regarded as a X direction, the up-down direction (vertical direction) is regarded as a Y direction, and the front-back direction (depth direction) is regarded as a Z direction. The X direction, the Y direction, and the Z direction define a three-dimensional orthogonal coordinate system.

First Embodiment

<Configuration>
FIG. 1 shows a schematic configuration of an ophthalmologic apparatus according to a first embodiment. The ophthalmologic apparatus 1 scans the fundus Ef of the subject's eye E with light to acquire data of the subject's eye, and obtains an image of the fundus Ef based on the acquired data. In FIG. 1, a two-dimensional tomographic image of the fundus, a three-dimensional image of the fundus, or a front image of the fundus Ef is obtained.

The ophthalmologic apparatus 1 includes an optical system 2, a housing unit (container) 3 configured to house the optical system 2, a movement mechanism 4, a controller 5, an image forming unit 6, a data processor 7, a user interface (UI) unit 8, and a detector 9. The ophthalmologic apparatus 1 may include a driver 4D that drives the movement mechanism 4 under the control of the controller 5.

<Movement Mechanism>
The movement mechanism 4 moves the optical system 2 (housing unit 3). The movement mechanism 4 includes a XYZ movement mechanism 4A, a swing mechanisms 4B, and a tilt movement mechanism 4C. The XYZ movement mechanism 4A moves the optical system 2 in the X direction, the Y direction, and the Z direction. The swing mechanism 4B swirls (rotates) the optical system 2 in the horizontal direction with reference to a predetermined position (for example, pupil position) of the subject's eye E. Specifically, the swing mechanism 4B moves the optical system 2 in the horizontal direction along an arc-like trajectory. The swing mechanism 4B swirls the optical system 2 within a predetermined movement angle range. The tilt mechanism 4C swirls (rotates) the optical system 2 in the vertical direction with reference to a predetermined position (for example, pupil position) of the subject's eye E. Specifically, the tilt mechanism 4C moves the optical system 2 in the vertical direction along an arc-like trajectory. The tilt mechanism 4C swirls the optical system 2 within a predetermined movement angle range. The center of rotation is not limited to the pupil position. The center of rotation may be a position displaced from the pupil position within a range that does not hinder scanning of a posterior segment. A position within such the range is referred to as a "near position of the pupil position". It should be noted that the displacement of the near position with respect to the pupil position may be a displacement in an arbitrary direction in the XYZ space. Hereinafter, unless otherwise stated, the "pupil position" means the "pupil position or near position of the pupil position".

The XYZ movement mechanism 4A is used, for example, in a position matching (alignment) of the optical system 2 with respect to the subject's eye E and a tracking. Here, the tracking is to move the optical system 2 according to the movement of the subject's eye E. To perform tracking, alignment and focusing are performed in advance. The tracking is performed by moving the optical system 2 in real time according to the position and orientation of the subject's eye E based on the image obtained by imaging (movie shooting) the subject's eye E, thereby maintaining a suitable positional relationship in which alignment and focusing are adjusted.

The swing mechanism 4B and the tilt mechanism 4C are used for wide-range scan for the subject's eye E (fundus Ef) and imaging of the peripheral region of the fundus Ef. The swing mechanism 4B and the tilt mechanism 4C three-dimensionally swirls, for example, the optical system 2 around the pupil position within a predetermined movement angle range.

Such the movement mechanism 4 includes, for example, one or more holding members that hold the optical system 2 and one or more guide arms that are movably provided at arbitrary positions within the above movement angle range. The movement mechanism 4 slides along the guide arm. It should be noted that the dimension of the rotating direction is not limited to three dimensions. The dimension of the rotating direction may be one dimension or two dimension, for example.

The driver 4D operates, for example, under the control of the controller 5. In this case, the driver 4D includes an actuator (not shown) that generates a driving force for rotating the optical system 2. The actuator generates the driving force corresponding to a control signal from the controller 5. This driving force is transmitted by a transmission mechanism (not shown). Thereby, the holding member can be moved along the guide arm. Using such control, the optical system 2 is rotated in the direction corresponding to the control signal by the angle corresponding to the control signal. In this case, a position of the optical system 2 is specified by the control content of the driver 4D by the controller 5. The specified position information is used by the controller 5, the image forming unit 6, the data processor 7, and the like.

Further, the movement mechanism 4 may not include the actuator. In this case, the optical system 2 is rotated manually. The position of the optical system 2 is detected by an encoder or a position sensor. Thereby, the acquired position information is used by the controller 5, the image forming unit 6, the data processor 7, and the like, for example.

The movement mechanism 4 may move the optical system 2 by moving the housing unit 3. The movement mechanism 4 may move only a part of the optical system 2.

<Attachment Member>
In the ophthalmologic apparatus 1, an attachment member 90 is provided between the housing unit 3 (optical system 2) and the subject's eye E. The attachment member 90 is configured to be detachable between the housing unit 3 and the eye E. For example, the attachment member 90 may be detachable with respect to the housing unit 3. The attachment member 90 includes a holding member 91. In the holding member 91, a passing part 92 through which an optical axis O of the optical system 2 passes is formed. The subject's eye E is disposed on the optical axis O that passed through the passing part 92. The holding member 91 holds a face of the subject movably in a state where a peripheral site Er (for example, upper site of the eye, or cheek) of the subject's eye E on the surface opposite to the apparatus side of the attachment member 90. The passing part 92 is, for example, a hole part formed so as to penetrate from the front surface to the back surface of the holding member 91. At the hole part, a transparent protective member or an optical member for protecting the subject's eye E may be disposed. That is, the subject brings a part of his/her face into contact with the holding member 91 so that the subject's eye E can visually recognize the side of the optical system 2 through the passing part 92. The measurement of the subject's eye E is performed in this state.

The holding member 91 has elasticity in at least one direction of the Z direction (direction of the optical axis O of the optical system 2), the X direction, and the Y direction (directions intersecting the direction of the optical axis O) at least in a part where the peripheral site Er is contacted. That is, the holding member 91 allows the subject's eye E to move in at least one direction of the X direction, the Y direction, and the Z direction while holding the subject's eye E. In such the holding member 91, an elastic member such as resin or rubber is provided at least at a part (face contact part) where the peripheral part Er is in contact. Thereby, the subject can change a position of the subject's eye E with respect to the optical system 2 by himself/herself while a part of the face is brought into contact with the holding member 91.

The holding member 91 has a thickness in the direction of the optical axis O such that the subject's eye E is disposed at a position corresponding to the working distance of the optical system 2 when the peripheral site Er is in contact with the holding member 91. For example, the holding member 91 has a thickness in the direction of the optical axis O so as not to approach the optical system 2 from a predetermined subject's eye position in a state where the subject brings the face into contact with the holding member 91. Here, the predetermined subject's eye position is uniquely determined by the positional relationship of the external shape of the housing unit 3 with respect to a reference position in the optical system 2 and the working distance of the optical system 2. Thereby, even if the working distance is short, the possibility of contact between the subject (a part of the face, subject's eye E) and the apparatus (optical system 2, housing unit 3) can be further reduced.

<Optical System>

The optical system 2 includes an optical member and a mechanism for optically acquiring data of the fundus (Ef). The optical system 2 includes an illumination optical system 10, an observation optical system 20, a scan optical system 30, an interference optical system 40, and a fixation optical system 50. The optical system 2 may include, for example, at least one of an alignment system for performing alignment of the optical system 2 with respect to the subject's eye E and a focus system for performing focus of the optical system 2 with respect to the subject's eye E.

The optical system 2 includes an optical element as an optical path coupling/separating member for separating the optical path of the optical system described above or coupling with another optical system. In FIG. 1, for example, beam splitters M1 to M3 are provided as the optical path coupling/separating members.

The beam splitter M1 couples an optical path of the illumination optical system 10 and an optical path of the observation optical system 20, or separates the optical path of the observation optical system 20 from an optical path of light transmitted through the beam splitter M2. The beam splitter M1 has a characteristic of transmitting light from the illumination optical system 10, and of reflecting light transmitted through the beam splitter M2 toward the observation optical system 20. It is preferred that the beam splitter M1 couples the illumination optical system 10 and the observation optical system 20 so that the optical axis of the illumination optical system 10 is substantially coaxial with the optical axis of the observation optical system 20.

The beam splitter M2 couples an optical path of the scan optical system 30 (or the interference optical system 40) and the optical path of the illumination optical system 10 (or the observation optical system 20), or separates the optical path of the scan optical system 30 (or the interference optical system 40) and the optical path of the illumination optical system 10 (or the observation optical system 20) from an optical path of light reflected by the beam splitter M3. The beam splitter M2 has a characteristic of transmitting light from the beam splitter M1, of reflecting light from the scan optical system 30 toward the beam splitter M3, of reflecting returning light, which returns from the subject's eye E, of light from the scan optical system 30 toward to the scan optical system 30, and of transmitting returning light, which returns from the subject's eye E, of light from the illumination optical system 10. It is preferred that the beam splitter M2 couples the scan optical system 30 (or the interference optical system 40) and the illumination optical system 10 (or observation optical system 20) so that the optical axis of the scan optical system 30 is substantially coaxial with the optical axis of the illumination optical system 10.

The beam splitter M3 couples an optical path of the fixation optical system 50 and the optical paths of the other optical systems. The beam splitter M3 has a characteristic of transmitting light from the fixation optical system 5, and of reflecting light from the other optical systems (the illumination optical system 10 and the interference optical system 40) or returning light thereof. It is preferred that the beam splitter M3 couples the fixation light optical system 50 and the other optical systems so that the optical axis of the fixation optical system 50 is substantially coaxial with the optical axes of the other optical systems.

In FIG. 1, an objective lens (not illustrated) is located between the beam splitter M3 and the subject's eye E.

(Illumination Optical System)

The illumination optical system 10 illuminates an anterior segment of the subject's eye E. The illumination optical system 10 includes an illumination light source, a lens, and the like.

(Observation optical system)

The observation optical system 20 is used for observing the anterior segment of the subject's eye E illuminated by the illumination optical system 10. The observation optical system 20 includes at least one of an eyepiece and an imaging element. The eyepiece is used for observing the subject's eye with the naked eye(s). The imaging element is used for acquiring a front image of the subject's eye E.

Illumination light from the illumination optical system 10 is transmitted through the beam splitters M1, M2, is reflected by the beam splitter M3, and passes through the objective lens (not shown) to illuminate the anterior segment of the subject's eye E. Returning light of the illumination light from the subject's eye E travels on the same path in the opposite direction, is reflected by the beam splitter M1, and enters the observation optical system 20. The returning light entered the observation optical system 20 is focused on an imaging surface of the imaging element, for example. The controller 5 that has received a signal from the imaging element controls the UI unit 8 to display the image acquired using the imaging element on a display unit (not shown) or the like.

(Scan Optical System)

The scan optical system 30 deflects measurement light output from the interference optical system 40 under the control of the controller 5. For example, the scan optical system 30 deflects light within a two-dimensional deflection angle range. It should be noted that the dimension of the deflecting direction is not limited to two dimensions. The dimension of the deflecting direction may be one dimension, for example.

The scan optical system 30 includes an optical scanner. A uniaxial deflecting member or a biaxial deflecting member is used as the optical scanner. Deflecting directions of the biaxial deflecting member are orthogonal to each other. Examples of the deflecting member include a galvano mirror, a polygon mirror, a rotating mirror, a dove prism, a double dove prism, a rotation prism, and a MEMS mirror scanner. When the biaxial deflecting member is used, a deflecting member for high speed scanning (for example, the polygon mirror) and a deflecting member for low speed scanning (for example, the galvano mirror) can be combined. The scan optical system 30 may further include an optical element for projecting the deflected light onto the fundus Ef.

(Interference Optical System)

The interference optical system 40 is configured to split light from a light source into measurement light and reference light, to project the measurement light onto the subject's eye E (fundus Ef), and to guide interference light, which is obtained by superimposing returning light of the measurement light from the subject's eye E and the reference light, to a detector. For the interference optical system 40, for example, a swept source type or a spectral domain type OCT (Optical Coherence Tomography) is applied.

When the swept source type OCT is applied, the interference optical system 40 includes an OCT light source. The OCT light source is a wavelength sweeping type (i.e., a wavelength scanning type) light source capable of sweeping (scanning) the wavelengths of emitted light. For example, a laser light source, which includes a resonator and emits light having a predetermined center wavelength, is used as the wavelength sweeping type light source. The wavelength sweeping type light source temporally changes the output wavelength in the near infrared wavelength band which cannot be visually recognized by the human eye.

Light output from the OCT light source may be, for example, near infrared light having a center wavelength of about 1040 nm to 1060 nm (for example, 1050 nm) and a wavelength width of about 50 nm. In the embodiments, the swept source type is particularly described. However, when the spectral spectral domain type OCT is applied, a light output device, such as a super luminescent diode (SLD), an LED, a semiconductor optical amplifier (SOA), or the like is used as the light source. Generally, the configuration of the OCT light source is selected as appropriate according to the type of optical coherence tomography.

Light output from the OCT light source is guided through an optical fiber to a fiber coupler, and is divided into the measurement light and the reference light. The measurement light is guided through an optical fiber, is emitted from the end of the fiber, and is collimated into a parallel light flux by a collimator lens. The end of this optical fiber is located at the fundus conjugate position or near the position. The fundus conjugate position is optically conjugate with the fundus Ef of the subject's eye E. The measurement light is deflected by the scan optical system 30, is reflected by the beam splitter M2, and is reflected by the beam splitter M3 toward the subject's eye E. The measurement light irradiated onto the fundus Ef is scattered and reflected at, for example, the measurement site(s) such as the fundus Ef. The scattered and reflected light may be sometimes referred to as returning light of the measurement light. The returning light of the measurement light travels through the same path in the opposite direction, and is thereby guided to the fiber coupler described above.

On the other hand, the reference light is guided through an optical fiber, is reflected by a reference mirror movable along the optical path of the reference light. The reflected light is again guided to the fiber coupler described above. It should be noted that a polarization adjuster (polarization controller), an optical element for dispersion compensation (pair prism, etc.), an optical element for polarization correction (wavelength plate, etc.), or an optical attenuator (attenuator) may be provided on the optical path of the reference light. The optical attenuator adjusts the amount of the reference light passing through the optical fiber under the control of the controller 5. The polarization adjuster applies external stress to the looped optical fiber to thereby adjust the polarization condition of the reference light guided through the optical fiber.

The returning light of the measurement light and the reference light reflected by the reference mirror enter the fiber coupler described above. The fiber coupler superposes the returning light of the measuring light on the reference light. Interference light thus generated is guided to a detector through an optical fiber. At this time, a pair of interference light is generated by another fiber coupler that generates the pair of interference light by branching the interference light at a predetermined branching ratio (for example, 1:1). The pair of interference light is detected by the detector (balanced photodiode). It should be noted that the detector (spectrometer) detects the interference light generated by the fiber coupler by decomposing it into a plurality of wavelength components in the case of spectral domain OCT.

The detector sends a detection result (detection signal) of the pair of interference light to a data acquisition system (DAQ) (not shown). The DAQ is fed with a clock from the OCT light source. This clock is generated in synchronization with the output timing of each wavelength swept within a predetermined wavelength range by the wavelength sweep type light source. The DAQ performs sampling of the detection signal based on the clock. The sampling result is sent to the image forming unit 6 for forming an OCT image.

(Fixation Optical System)

The fixation optical system 50 projects fixation light flux onto the fundus Ef of the subject's eye E. Such the fixation optical system 50 includes, for example, a fixation light source that outputs visible light or a display device such as a liquid crystal display that displays a visual target in response to an instruction from the controller 5.

The optical system 2 may be provided with an alignment system and/or a focus system. The alignment system or the focus system includes an optical system for projecting an index (alignment index, focusing index) onto the subject's eye E and an optical system for detecting returning light thereof, as in the conventional configuration. In addition, two or more imaging devices that image the anterior segment of the subject's eye E can be provided. In this case, alignment is performed by analyzing two or more anterior segment images acquired substantially simultaneously by these imaging devices (for example, using trigonometry).

<Regarding Scan>

In the optical system 2 as described above, for example, the measurement light generated based on the OCT light source in the interference optical system 40 is deflected by the scan optical system 30 and is imaged as spot light on the fundus Ef through the pupil of the subject's eye E. The returning light is light that returns from a projection position of the spot light (or in the vicinity of the position) to the optical system 2. The returning light is guided through the fiber coupler as described above, and is superposed with the reference light. This interference light between the returning light of the measurement light and the reference light is detected by the detector. The detector generates an electrical signal (light reception signal) by photoelectric conversion. In addition, the projection position of the spot light may be described as a spot position.

This series of processes corresponds to measurement of one point of the fundus Ef. The scan optical system 30 moves the spot position within the predetermined deflection angle range. That is, the scan within the predetermined deflection angle range is realized by the scan optical system 30. Further, the movement mechanism 4 rotates the optical system 2 within the predetermined movement angle range. That is, the movement mechanism 4 moves a scan area (single scan area) corresponding to the deflection angle range of the scan optical system 30. By combining these, a wide range of the fundus Ef can be measured while moving the single scan area.

Figure 2:
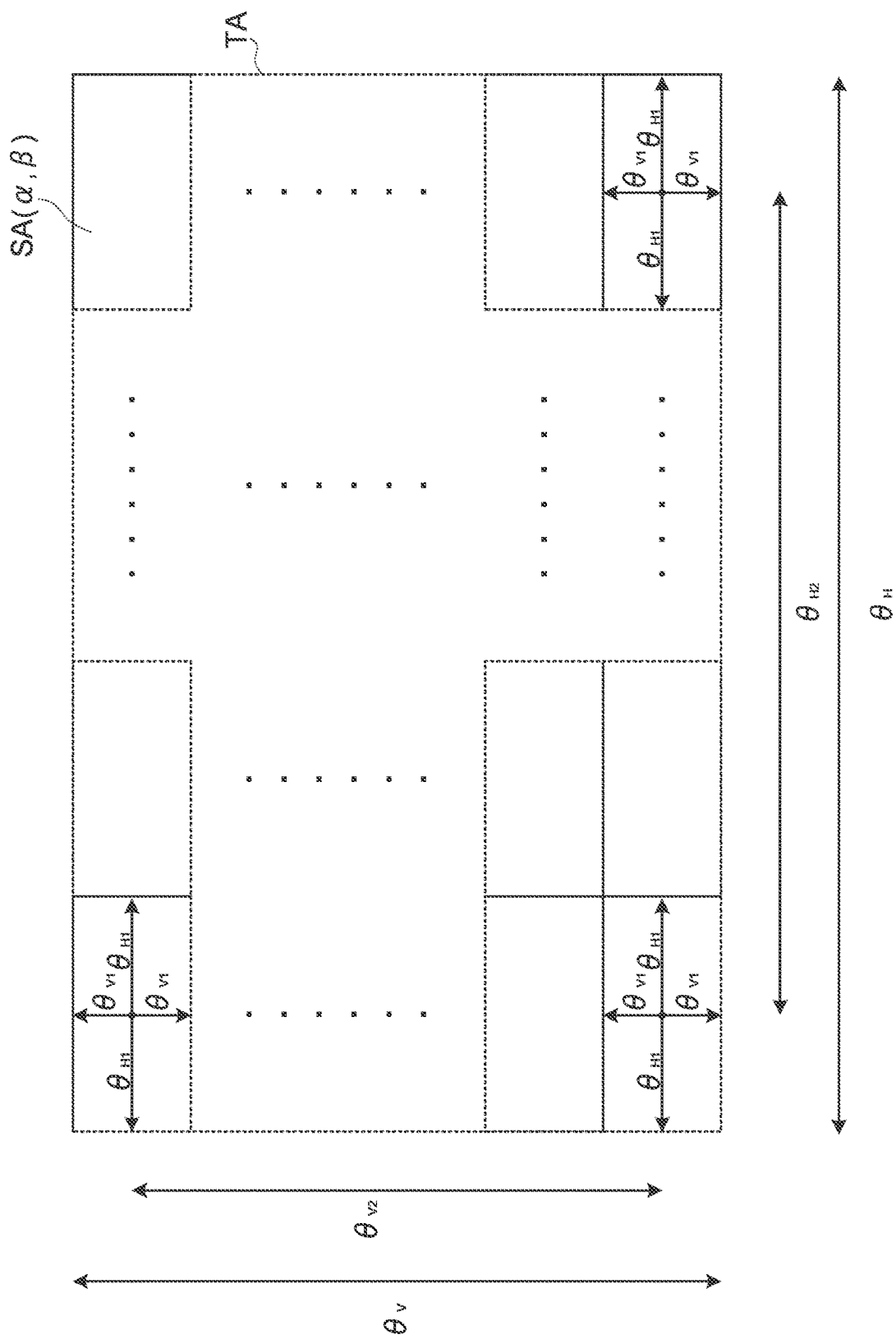
FIG. 2 is a schematic diagram for explaining an operation of the ophthalmologic apparatus according to the embodiments.

FIG. 2 shows a diagram describing the scan operation in the ophthalmologic apparatus 1 according to the embodiments.

As shown in FIG. 2, an entire scan area TA includes one or more sub-scan areas SA ($\alpha$, $\beta$). The range in the horizontal direction (for example, the X direction) of the entire scan area TA is defined as $\theta$H. The range in the vertical direction (for example, the Y direction) of the entire scan areas TA is defined as $\theta$V. The entire scan area TA is divided into a plurality of sub-scan areas SA ($\alpha$, $\beta$) arranged vertically and horizontally. Here, $\alpha$=1, 2, . . . , M and $\beta$=1, 2, . . . , N. M and N are each an integer of 1 or more, and at least one of M and N is an integer of 2 or more. In addition, it is not necessary that all of the plurality of sub-scan areas SA ($\alpha$, $\beta$) have the same size. It is not necessary that all of the plurality of sub-scan areas SA ($\alpha$, $\beta$) have the same shape.

Each sub-scan area SA ($\alpha$, $\beta$) corresponds to the single scan area. A part of the sub-scan area SA ($\alpha$, $\beta$) and a part of the sub-scan area SA ($\alpha$+1, $\beta$) may overlap. A part of the sub-scan area SA ($\alpha$, $\beta$) and a part of the sub-scan area SA ($\alpha$, $\beta$+1) may overlap.

In the embodiments, by scanning a plurality of sub-scan areas SA ($\alpha$, $\beta$) sequentially, scanning of the entire scan area TA is realized. By controlling the scan optical system 30, scanning of each sub-scan area SA ($\alpha$, $\beta$) is performed. By controlling the movement mechanism 4, the sub-scan area SA ($\alpha$, $\beta$) to be scanned is changed.

A scan of each sub-scan area SA ($\alpha$, $\beta$) will be described. For example, the scan optical system 30 deflects the measurement light from the interference optical system 40 within the predetermined deflection angle range. The range in the horizontal direction of this deflection angle range is defined as "2·$\theta$H1". The range in the vertical direction of this deflection angle range is defined as "2·$\theta$V1". That is, the scan optical system 30 can move the spot position by "$\theta$H1" in the left-right direction with reference to a center of the deflection center (for example, the position on the optical axis of the scan optical system 30). The scan optical system 30 can move the spot position by "$\theta$V1" in the up-down direction with reference to the center of the deflection. The deflection angle and the distance (chord length) in the XY plane correspond to each other. Thereby, they can be regarded as the same.

The sub-scan area SA ($\alpha$, $\beta$) is switched by rotating the optical system 2 within the predetermined movement angle range around the pupil position by the movement mechanism 4. The range in the horizontal direction of this movement angle range is defined as "$\theta$H2". The range in the vertical direction of this movement angle range is defined as "$\theta$V2". That is, the movement mechanism 4 can rotate the optical system 2 by "$\theta$H2" in the horizontal direction. The movement mechanism 4 can rotate the optical system 2 by "$\theta$V2" in vertical direction.

According to the scan optical system 30 and the movement mechanism 4 as described above, when the plurality of sub-scan areas SA ($\alpha$, $\beta$) are arranged without overlapping or gaps, the movement range of the spot position in the horizontal direction is $\theta$H=$\theta$H2+2·$\theta$H1, and the movement range of the spot position in the vertical direction is $\theta$V=$\theta$V2+2·$\theta$V1. An area where the range in the horizontal direction is $\theta$H and the range in the vertical direction is $\theta$V corresponds to the entire scan area TA. It should be noted that when an overlap or a gap is provided, the entire scan area TA is determined according to the overlap width and the gap interval.

In one example, $\theta$H1=60 degrees, $\theta$H2=40 degrees, $\theta$V1=40 degrees, and $\theta$V2=40 degrees are set. Thereby, a range of 160 degrees in the horizontal direction and 120 degrees in the vertical direction can be scanned. It should be noted that $\theta$H1, $\theta$H2, $\theta$V1, and $\theta$V2 are determined in consideration of arbitrary factors such as cost and working distance.

<Controller>

The controller 5 controls each part of the apparatus. The controller 5 includes a processor and a storage device (storage circuit). The storage device stores in advance computer programs for controlling the ophthalmologic apparatus 1. The computer programs include a light source control program, a scan control program, a movement mechanism control program, a user interface control program, and the like. The processor operates under these computer programs, and thereby the controller 5 performs the control operation.

The "processor" includes a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA).

In the embodiments, by controlling the scan optical system 30 and the movement mechanism 4 in liaison with each other, scan as illustrated in FIG. 2 can be realized. For example, the storage device in the controller 5 stores in advance a previously defined deflection pattern for deflecting the measurement light and a previously defined movement pattern for moving the optical system 2. The deflection pattern and/or the movement pattern may be set by default or may be set by the user. In addition, a plurality of deflection patterns and a plurality of movement patterns may be applied in any combination. The selection of the pattern is performed by, for example, the user or the controller 5.

The controller 5 executes the control (scan control) of the scan optical system 30 based on the deflection pattern and the control (movement control) of the movement mechanism 4 based on the movement pattern in liaison with each other. For example, the controller 5 executes the scan control and the movement control alternately. Here, a single scan control corresponds to scanning a single scan area (one sub-scan area). A single movement control corresponds to switching sub-scan areas. As another example, the controller 5 can perform scan control and movement control in parallel in at least some phases of scanning for the entire scan area.

Figure 3:
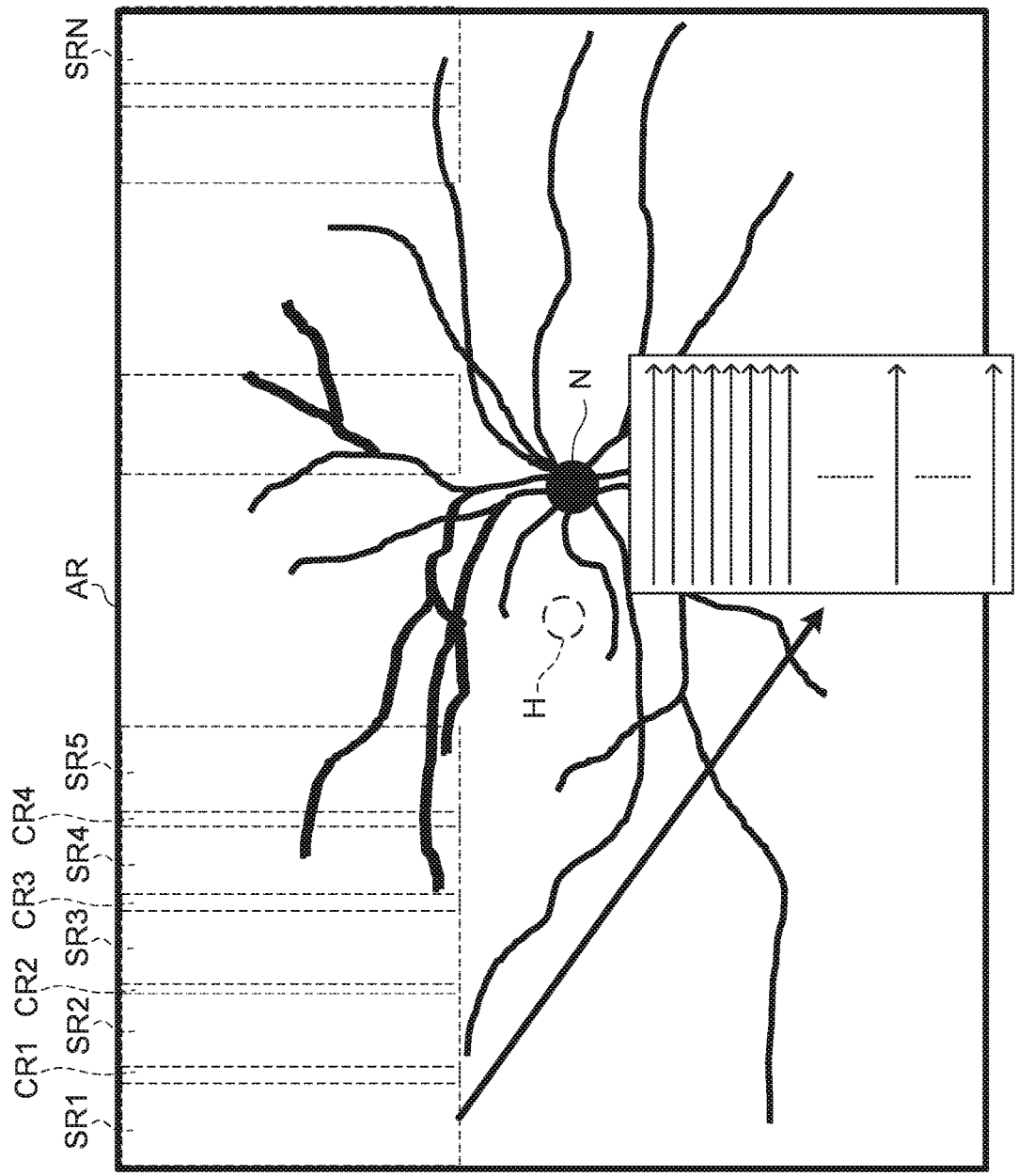
FIG. 3 is a schematic diagram for explaining an operation of the ophthalmologic apparatus according to the embodiments.

FIG. 3 shows a diagram describing a scan mode according to the embodiments. FIG. 3 schematically represents a mode in which the entire scan area AR including the optic disc N and the macular region H is divided into a plurality of sub-scan areas and scanned.

The controller 5 moves the sub-scan area (single scan area) to be scanned by controlling the movement mechanism 4 in accordance with the previously defined movement pattern. For example, the controller 5 moves the sub-scan area to be scanned in the order of, for example, sub-scan areas SR1, SR2, SR3, . . . . At this time, adjacent sub-scan areas SRi and SR (i+1) have an overlapping area CRi (i=1, 2, 3, . . . ). When an image of the entire scan area AR is formed from a plurality of images obtained from a plurality of sub-scan areas, position matching of adjacent images can be performed using the overlapping area. The controller 5 controls the optical system 2 so as to scan each sub-scan area based on the previously defined deflection pattern. In the example shown in FIG. 3, a raster scan is applied. Other examples of the deflection pattern include circle scan, concentric circle scan, radial scan, slit scan (one dimensional scan), and the like.

<Image Forming Unit>

The image forming unit 6 includes a storage device that stores a program for forming image and a processor that operates in accordance with the program for forming image. The image forming unit 6 forms a tomographic image of the fundus Ef based on the detection signal (light receiving signal) input from the detector and a pixel position signal input from the controller 5, for example as is the case with conventional OCT. For example, the image forming unit 6 can apply Fourier transform and the like to the spectral distribution based on the detection result of the interference light, for example, every series of wavelength scans (every A-line) to form the reflection intensity profile in each A-line. The image forming unit 6 can form image data by imaging the reflection intensity profile in each A-line.

<Data Processor>

The data processor 7 executes various data processing. Examples of the data processing include processing on the image data formed by the image forming unit 6 or another apparatus. Examples of this processing include image processing, image analyzing, image evaluation, diagnosis support, and the like. For example, the data processor 7 performs correction processing such as brightness correction of images and/or dispersion correction of images. Further, the data processor 7 performs various kinds of image processing and various kinds of analysis processing on fundus images or tomographic images. The data processor 7 can form volume data (voxel data) of the subject's eye E by performing known image processing such as interpolation processing for interpolating pixels between tomographic images. In the case of displaying an image based on the volume data, the data processor 7 performs rendering processing on the volume data so as to form a pseudo three-dimensional image viewed from a specific line-of-sight direction.

In addition, the data processor 7 can a C-mode image, a projection image, a shadowgram, or the like from the volume data. The C-mode image is formed by selecting pixels (voxels) on a designated cross section from the three-dimensional data set. The projection image is formed by projecting the three-dimensional data set in a predetermined direction (Z direction, depth direction, axial direction). The shadowgram is formed by projecting a part of the three-dimensional data set (for example, partial data corresponding to a specific layer) in a predetermined direction.

Further, the data processor 7 can form an image of the entire scan area AR by performing position matching of adjacent images on a plurality of images (tomographic images) obtained from a plurality of sub-scan areas. At this time, the data processor 7 can perform position matching of adjacent images using the overlapping area.

The data processor 7 includes a storage device that stores a program for data processing and a processor that operates in accordance with the program for data processing.

<User Interface Unit>

The user interface (UI) unit 8 has a function for exchanging information between a user and the ophthalmologic apparatus 1. The user interface unit 8 includes a display device and an operation device (an input device). The display device includes, for example, a liquid crystal display (LCD). The operation device includes various hardware keys and/or various software keys. Upon receiving the operation content for the operation device, the controller 5 can output a control signal corresponding to the operation content to each part of the ophthalmologic apparatus 1. At least a part of the display device and at least a part of the operation device may be configured integrally. One example of this is the touch panel display.

<Detector>

The detector detects whether or not the attachment member 90 is attached to the ophthalmologic apparatus 1 (for example, the housing unit 3). Examples of such the detection unit 9 include a microswitch that is pressed down by the attachment member 90 in a state where the attachment member 90 is attached to the ophthalmologic apparatus 1. Further, the attachment state of the attachment member 90 may be detected by a known detection method using a contact sensor or an optical sensor.

Further, the detector 9 may detect the attachment state of the attachment member 90 with respect to the ophthalmologic apparatus 1 by user operation using the UI unit 8. For example, a user designates that the attachment member 90 is attached or designates that the attachment member 90 is not attached, by operation on the UI unit 8.

Such the detection result by the detection unit 9 is output to the controller 5. The ophthalmologic apparatus 1 according to the embodiments is capable of changing alignment operation mode depending on the detection result of the detector 9. That is, the controller 5 can control the driver 4D based on the detection result obtained by the detector 9. Specifically, the ophthalmologic apparatus 1 performs a first alignment operation for performing auto alignment, when it is detected by the detector 9 that the attachment member is not attached. In addition, the ophthalmologic apparatus 1 performs a second alignment operation for performing alignment by the subject himself (herself), when it is detected by the detector that the attachment member is attached. During performing the second alignment operation, the controller 5 inhibits the movement of the optical system 2 by the movement mechanism 4. Thereby, while avoiding unintended contact between the subject's face and the ophthalmologic apparatus 1, the position of the subject's eye E with respect to the optical system 2 can be easily adjusted by the subject himself/herself.

<Other Controls>

In case that the moving image photographing (infrared moving image observation or the like) of the fundus Ef can be performed, the controller 5 can perform tracking control for compensation for eye movement so that a predetermined site of the fundus Ef is depicted at a constant position in the image (frame) while monitoring the movement of the fundus Ef. Further, the controller 5 or the data processor 7 can perform tracking afterwards by correcting the displacement of the depicted position between images (between frames), the displacement being obtained by analyzing the acquired data. Further, the controller 5 or the data processor 7 can detect an eye direction of the subject's eye E to perform tracking control so as to cancel displacement of the position by the movement of eye direction.

The Z direction is an example of the "direction of the optical axis" according to the embodiments. The X direction or the Y direction is an example of the "direction intersecting the direction of the optical axis" according to the embodiments.

Operation Example

An example of the operation of the ophthalmologic apparatus 1 according to the first embodiment will be described.

Figure 4:
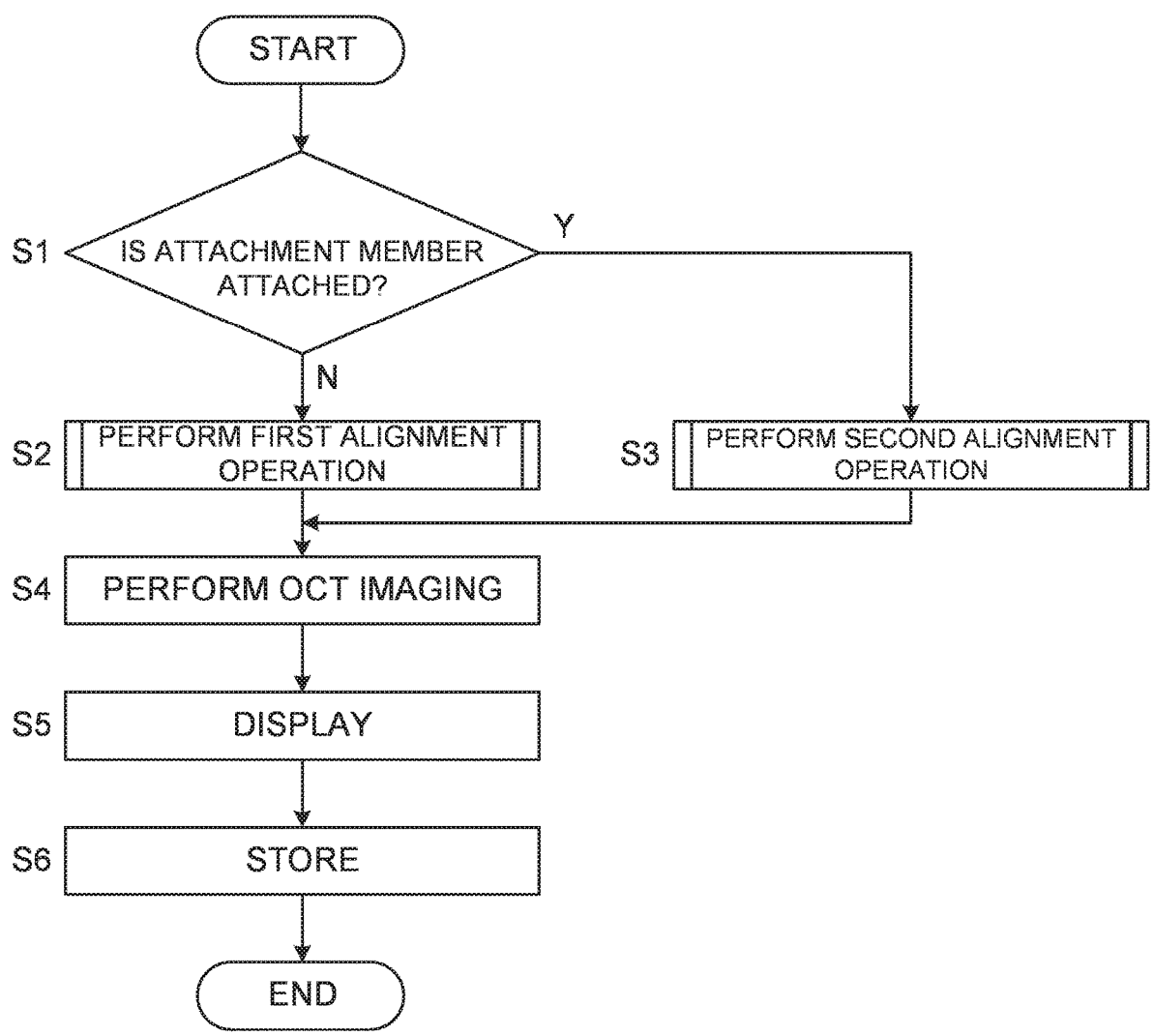
FIG. 4 is a schematic diagram for explaining an operation of the ophthalmologic apparatus according to the embodiments.
Figure 5:
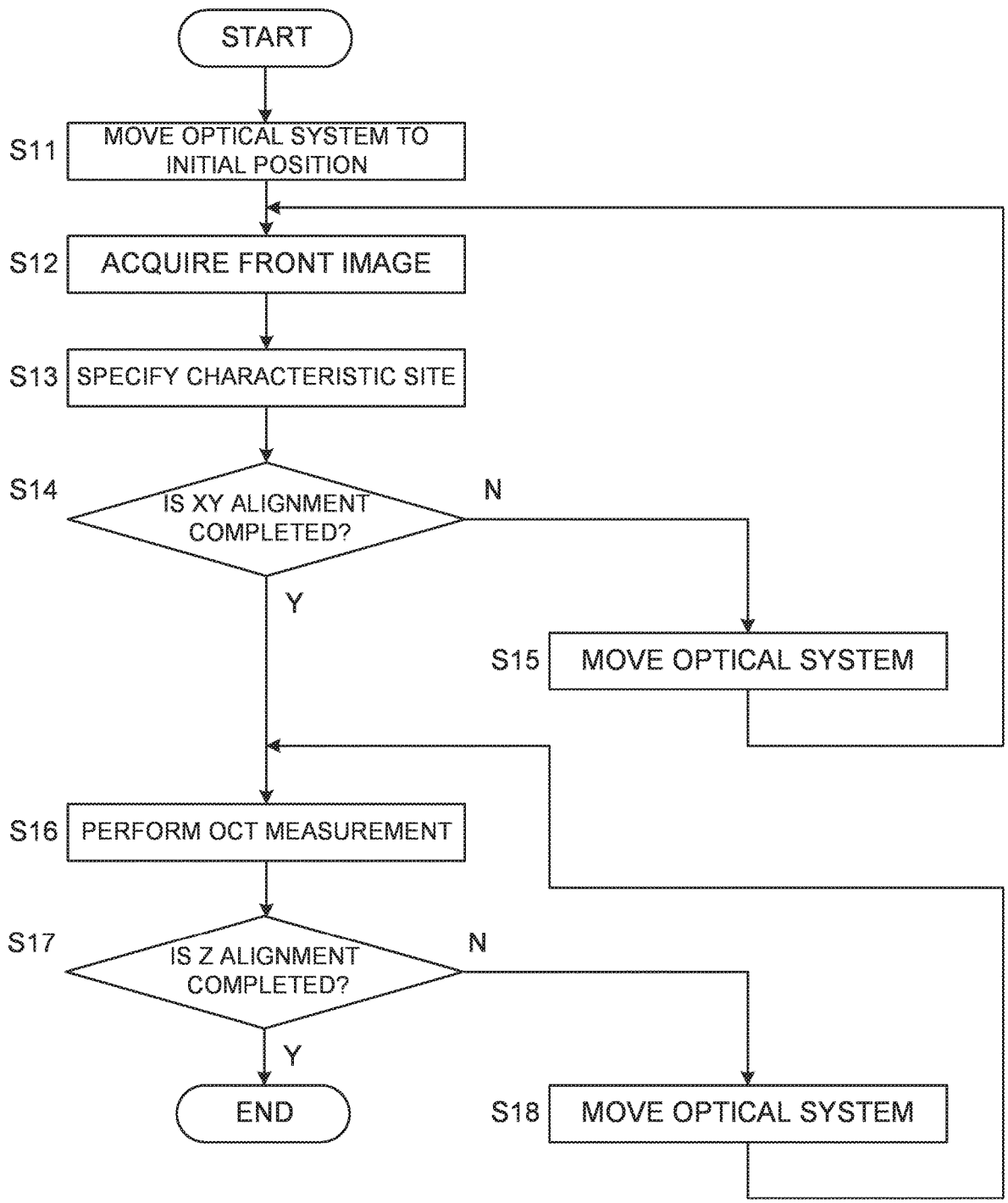
FIG. 5 is a flowchart illustrating an example of an operation of the ophthalmologic apparatus of the embodiments.
Figure 6:
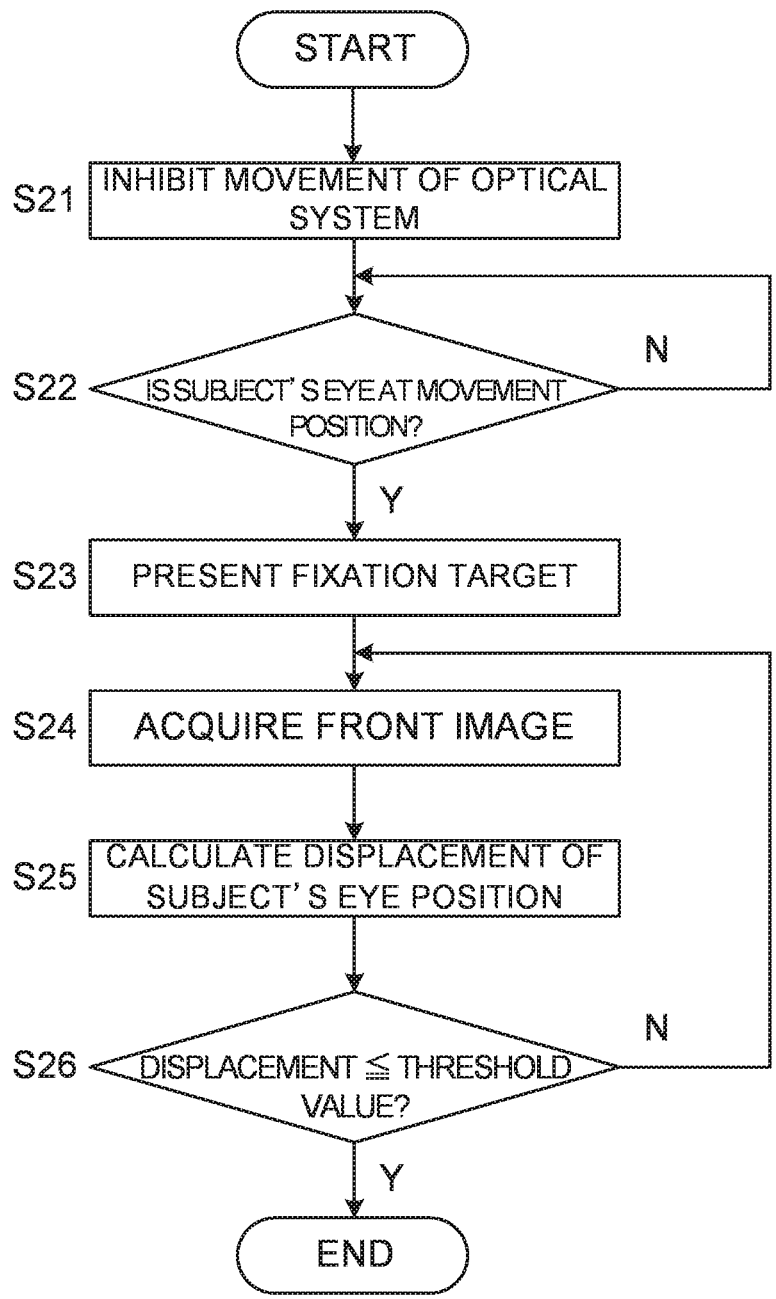
FIG. 6 is a flowchart illustrating an example of an operation of the ophthalmologic apparatus according to the embodiments.

FIGS. 4 to 6 show flowcharts of examples of the operation of the ophthalmologic apparatus 1 according to the first embodiment. FIG. 4 represents a flowchart of an example of the operation when OCT imaging is performed by the ophthalmologic apparatus 1. FIG. 5 represents a flowchart of an example of the operation of the first alignment operation in step S2 of FIG. 4. FIG. 6 shows a flowchart of an example of the operation of the second alignment operation in step S3 in FIG. 4.

(S1) First, the controller 5 determines whether or not the attachment member 90 is attached to the ophthalmologic apparatus 1. The controller 5 determines whether or not the attachment unit 90 is attached based on the detection result obtained by the detector 9. When it is determined that the attachment member 90 is not attached (S1: N), the operation of the ophthalmologic apparatus 1 proceeds to step S2. When it is determined that the attachment member 90 is attached (S1: Y), the operation of the ophthalmologic apparatus 1 proceeds to step S3.

(S2) In step S1, when it is determined that the attachment member 90 is not attached (S1: N), the controller 5 performs the first alignment operation. The first alignment operation will be described later. And then, the operation of the ophthalmologic apparatus 1 proceeds to step S4.

(S3) In step S1, when it is determined that the attachment member 90 is attached (S1: Y), the controller 5 performs the second alignment operation. The second alignment operation will be described later. And then, the operation of the ophthalmologic apparatus 1 proceeds to step S4.

(S4) When the first alignment operation or the second alignment operation is completed, the controller 5 performs OCT imaging. In the OCT imaging, as described above, the light from the OCT light source is split into the measurement light and the reference light. The measurement light is projected onto the subject's eye E (fundus Ef). And, the interference light obtained by superposing the returning light of the measurement light from the subject's eye E and the reference light is detected by the detector. At this time, the measurement light is deflected by the scan optical system 30. In the embodiments, the controller 5 controls the scan optical system 30 and the movement mechanism 4 in liaison with each other, as described above. Thereby, the scan of the entire scan area can be performed while scanning a plurality of sub-scan areas as shown in FIG. 2 or FIG. 3. The controller 5 causes the image forming unit 6 to form the OCT image based on the detection result of the detector. For example, the image forming unit 6 can form the tomographic image of the predetermined site in the fundus Ef based on the scan result for the entire scan area shown in FIG. 2 or FIG. 3.

(S5) Subsequently, the controller 5 causes the display unit or the like in the UI unit 8 to display the tomographic image formed in step S4.

(S6) The controller 5 stores the image data of the tomographic image formed in step S4 in the storage device. This terminates the operation of the ophthalmologic apparatus 1 (END).

In step S2 of FIG. 4, in the first alignment operation, the XY alignment is performed based on the front image of the subject's eye E acquired by the observation optical system 20. And the Z alignment is performed based on the detection result of the interference light acquired by the interference optical system 40. The Z alignment is not limited to that performed based on information (detection result or the like) from the interference optical system 40. The Z alignment may be performed based on, for example, the contrast value of the image of the subject's eye E obtained by the observation optical system 20.

(S11) The controller 5 causes the movement mechanism 4 to move the optical system 2 to initial position(s). For example, the controller 5 controls the movement mechanism 4 so that the optical system 2 is disposed at a position for performing scan for a predetermined sub-scan area.

(S12) Subsequently, the controller 5 causes the illumination optical system 10 to illuminate the anterior segment of the subject's eye E by controlling the illumination optical system 10, and causes the observation optical system 20 to acquire the front image of the anterior segment of the subject's eye E.

(S13) Next, the controller 5 causes the data processor 7 to specify a characteristic site such as a region (pupil center region) corresponding to the pupil center from the illuminated image (front image) of the anterior segment obtained in step S12. For example, the data processor 7 can specify the pupil region based on the brightness of the acquired image, can specify the contour of the specified pupil region, and can obtain the center of the pupil region from the specified contour. The characteristic region (site) may be, for example, a region corresponding to the center of gravity of the pupil (region of the center of gravity of the pupil), a region corresponding to the iris center (iris center region), a region corresponding to the center of gravity of the iris (region of the center of gravity of the iris), and a region representing an iris pattern (iris pattern region).

(S14) The controller 5 determines whether or not a distance between a position of the characteristic site in the front image and a position corresponding to the optical axis O is within a predetermined threshold value. When it is determined that the distance is within the predetermined threshold value (S14: Y), it is determined that the XY alignment is completed and the operation of the ophthalmologic apparatus 1 proceeds to step S16. When it is determined that the distance exceeds the predetermined threshold value (S14: N), it is determined that the XY alignment is not completed and the operation of the ophthalmologic apparatus 1 proceeds to step S15.

(S15) When it is determined that the distance exceeds the predetermined threshold value in step S14 (S14: N), the controller 5 moves the optical system 2 (housing unit 3) in at least one of the X direction and the Y direction by controlling the driver 4D so as to coincide the characteristic site in the front image with the optical axis O of the optical system 2. And then, the operation of the ophthalmologic apparatus 1 proceeds to step S12.

(S16) When it is determined that the distance is within the predetermined threshold value in step S14 (S14: Y), the controller 5 starts the OCT measurement. Specifically, the controller 5 causes the interference optical system 40 to irradiate the fundus Ef of the subject's eye E with the measurement light. Thereby, in the interference optical system 40, the interference light is generated between the returning light of the measurement light from the fundus Ef and the reference light, and is detected by the detector. The controller 5 specifies the intensity of the interference light based on the detection result of the interference light obtained by the detector.

(S17) The controller 5 determines whether or not the intensity of the interference light specified in step S16 is equal to or greater than a predetermined threshold value. When it is determined that the intensity of the interference light is equal to or greater than the predetermined threshold value (S17: Y), it is determined that the Z alignment is completed and the first alignment operation terminates (END). When it is determined that the intensity of the interference light does not exceed the predetermined threshold value (S17: N), the operation of the ophthalmologic apparatus 1 proceeds to step S18.

(S18) When it is determined that the intensity of the interference light does not exceed the predetermined threshold value in step S17 (S17: N), the controller 5 moves the optical system 2 (housing unit 3) in the Z direction by controlling the driver 4D so that the intensity of the interference light becomes equal to or greater than the predetermined threshold value. The controller 5 may specify the movement direction and the movement amount of the optical system 2 from the intensity of the interference light specified in step S16, by referring to table information in which the intensity of the interference light is associated with the movement direction and the movement amount of the optical system 2 in advance. In this case, the table information is stored in the storage device. And then, the operation of the ophthalmologic apparatus 1 proceeds to step S16.

In step S3 of FIG. 4, in the second alignment operation, the position matching of the subject's eye E with respect to the optical system 2 is performed by moving the face by the subject himself/herself in a state where the movement of the optical system 2 by the movement mechanism 4 is inhibited.

(S21) First, the controller 5 performs control for inhibiting the movement of the optical system 2 by the movement mechanism 4. The controller 5 can perform control for inhibiting the movement of the optical system 2 by the movement mechanism 4 after controlling the movement mechanism 4 to move the optical system 2 to a reference position(s). This control for inhibiting may be, for example, invalidation control of control for the driver 4D, mechanical control for preventing the driving force from being transmitted to the movement mechanism 4, or inhibition control of the movement of optical system 2 from current position by the movement mechanism 4 using a stopper member.

(S22) Next, the controller 5 determines whether or not the subject's eye E is disposed at a predetermined measurement position. For example, the controller 5 caused the display unit of the UI unit 8 to display information or the like for prompting the subject to bring the face into contact with the holding member 91 so as to look into the optical system 2 side through the passing part 92. Thus, when the subject holds the face on the holding member 91, the subject's eye is arranged at the predetermined measurement position. The controller 5 can determine whether or not the subject's eye E is disposed at the predetermined measurement position when the subject having his/her face brought into contact with the holding member 91 performs an operation on the UI unit 8. Further, the controller 5 may determine whether or not the subject's eye E is disposed at the predetermined measurement position by detecting whether the face of the subject is held at a predetermined position of the holding member 91 by a sensor (not shown).

When it is determined that the subject's eye E is disposed at the predetermined measurement position (S22: Y), the operation of the ophthalmologic apparatus 1 proceeds to step S23. When it is not determined that the subject's eye E is disposed at the predetermined measurement position (S22: N), the ophthalmologic apparatus 1 repeats the process of step S22.

(S23) When it is determined that the subject's eye E is disposed at the predetermined measurement position in step S22 (S22: Y), the controller 5 controls the fixation optical system 50 to present a fixation target at a predetermined fixation position (for example, a previously defined origin position).

(S24) Subsequently, the controller 5 causes the illumination optical system 10 to illuminate the anterior segment of the subject's eye E by controlling the illumination optical system 10, and causes the observation optical system 20 to acquire the front image of the anterior segment of the subject's eye E.

(S25) Next, the controller 5 specifies a position of the subject's eye E (for example, a position of a characteristic site of the subject's eye E) from the front image of the anterior segment acquired in step S24, and obtains displacement of the position of the subject's eye E with respect to a predetermined reference position (for example, a position corresponding to the optical axis O). The displacement may be calculated by the data processor 7.

(S26) The controller 5 determines whether or not the displacement of the position of the subject's eye E obtained in step S25 is equal to or less than a predetermined threshold value. When it is determined that the displacement is equal to or less than the predetermined threshold value (S26: Y), the second alignment operation terminates (END).

When it is determined that the displacement exceeds the predetermined threshold value (S26: N), the operation of the ophthalmologic apparatus 1 proceeds to step S24. At this time, the controller 5 can cause the UI unit 8 to display information or the like for prompting the subject to move the position of the subject's eye E by moving his/her face. In addition, the information displayed on the display unit preferably includes information corresponding to the direction and/or the amount of movement to move the subject's eye E.

It should be noted that the examiner or the subject may designate whether the first alignment operation or the second alignment operation is performed, using the UI unit 8, in step S1 of FIG. 4. In addition, the controller 5 may determine whether the first alignment operation or the second alignment operation is performed, based on shape measurement data of the subject's face. For example, when it is determined that the subject's face is a chiseled face based on the shape measurement data, the controller 5 can designate the second alignment operation, thereby contacting between the subject and the apparatus can be avoided.

As described above, in the first embodiment, the alignment operation of the ophthalmologic apparatus 1 is changed depending on the attachment state of the attachment member 90 including the holding member 91 that holds the subject's face movably. When the attachment member 90 is not attached, the ophthalmologic apparatus 1 performs position matching of the subject's eye E with respect to the optical system 2 using so-called auto alignment. When the attachment member 90 is attached, the ophthalmologic apparatus 1 inhibits the movement of the optical system 2. In this case, the position matching of the subject's eye E with respect to the optical system 2 is performed by changing the position of the subject's eye E, by the movement of the subject himself/herself, whose face is held movably by the holding member 91. Thereby, contact between the subject and the ophthalmologic apparatus 1 can be avoided even in an ophthalmologic apparatus having a short working distance.

Second Embodiment

The ophthalmologic apparatus according to the embodiments can prompt to move the subject's eye E to an appropriate measurement position in the second alignment operation. Hereinafter, the ophthalmologic apparatus according to the second embodiment is described mainly about the differences from the first embodiment.

<Configuration>

Figure 7:
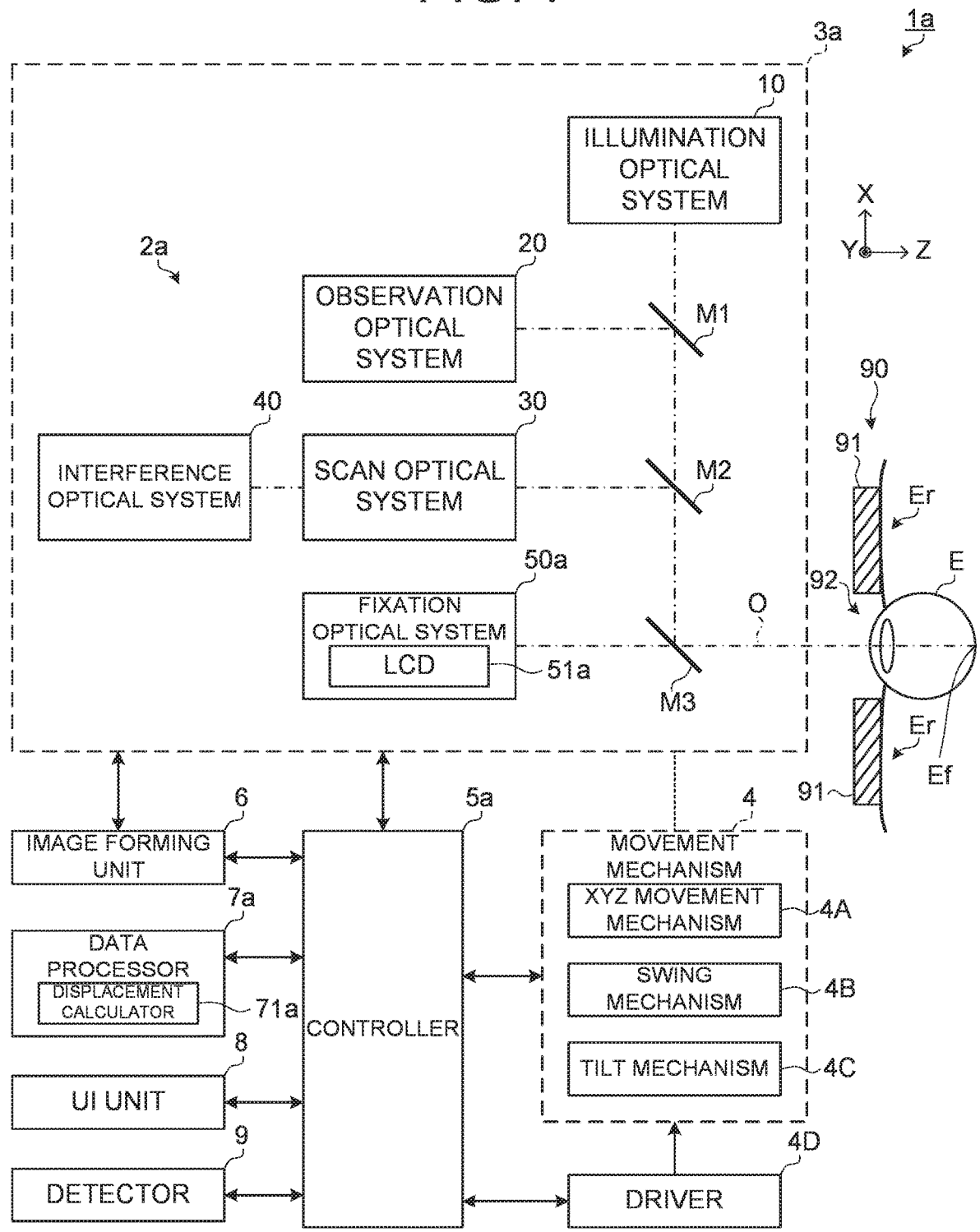
FIG. 7 is a schematic diagram illustrating an example of the configuration of the ophthalmologic apparatus according to the embodiments.

FIG. 7 shows a schematic configuration of the ophthalmologic apparatus according to the second embodiment. The difference between the configuration of the ophthalmologic apparatus 1a according to the second embodiment and the configuration of the ophthalmologic apparatus 1 according to the first embodiment is mainly that an optical system 2a is provided instead of the optical system 2, that a data processor 7a is provided instead of the data processor 7, and that a controller 5a is provided instead of the controller 5.

The difference between the configuration of the optical system 2a accommodated in the housing unit 3a and the configuration of the optical system 2 is mainly that a fixation optical system 50a is provided instead of the fixation optical system 50. The fixation optical system 50a includes a liquid crystal display 51a that displays a fixation target for presenting to the subject's eye E. The liquid crystal display 51a can display a desired visual target image (fixation image) under the control of the controller 5a. Further, the controller 5a can cause the fixation optical system 50a to function in the same manner as the fixation optical system 50, by displaying the visual target image corresponding to the fixation target on the liquid crystal display 51a.

The data processor 7a has a configuration in which a displacement calculator 71a is added to the configuration of the data processor 7. The displacement calculator 71a calculates displacement between the characteristic site and the position corresponding to the optical axis O in the front image of the subject's eye E acquired by the observation optical system 20. The controller 5a specifies a relative position of the subject's eye E with respect to the optical system 2a from the calculated displacement, and controls the fixation optical system 50a depending on the specified relative position. At this time, in order to cause the subject to recognize the direction and the amount of the movement of the subject's eye E, the data processor 7a (or the image forming unit 6) can generate the fixation image depending on the displacement.

The controller 5a can further control the fixation optical system 50a and the data processor 7a with respect to the control content of the control unit 5.

Operation Example

The difference between the operation of the ophthalmologic apparatus 1a according to the second embodiment and the operation of the ophthalmologic apparatus 1 according to the first embodiment is mainly the second alignment operation.

Figure 8:
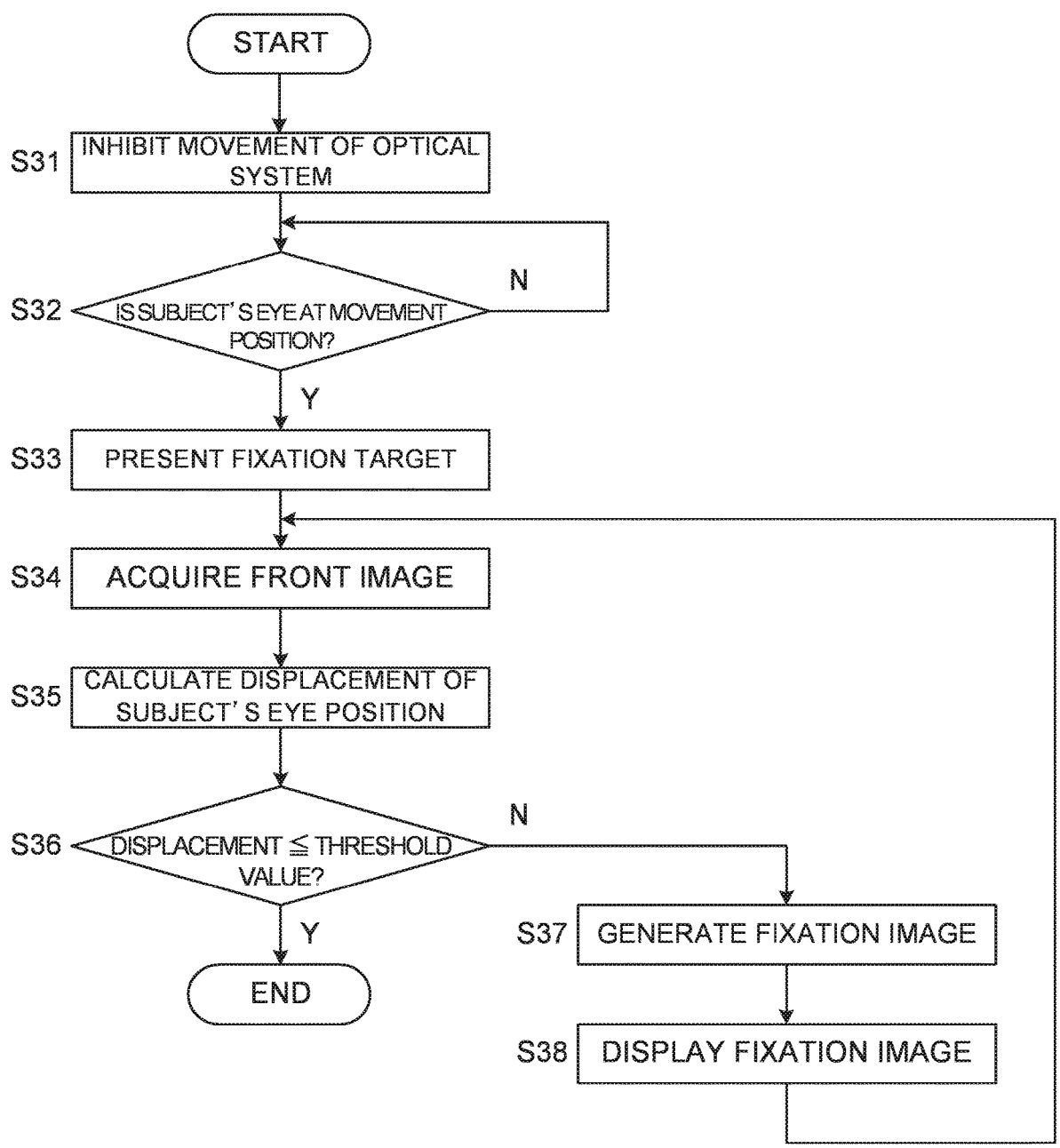
FIG. 8 is a flowchart illustrating an example of an operation of the ophthalmologic apparatus according to the embodiments.
Figure 9:
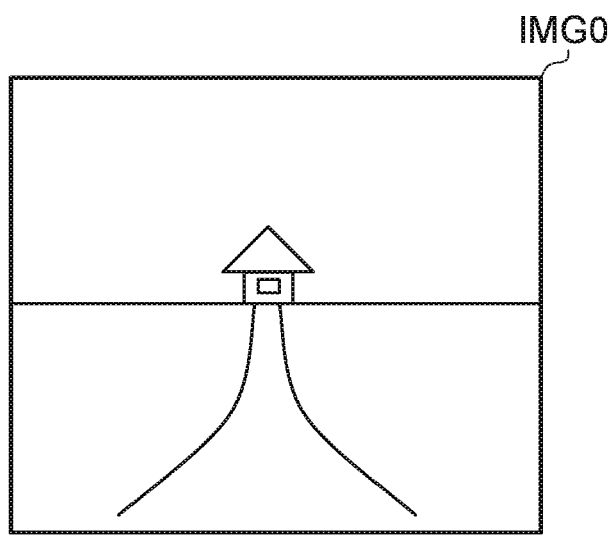
FIG. 9 is a schematic diagram for explaining an operation of the ophthalmologic apparatus according to the embodiments.
Figure 10:
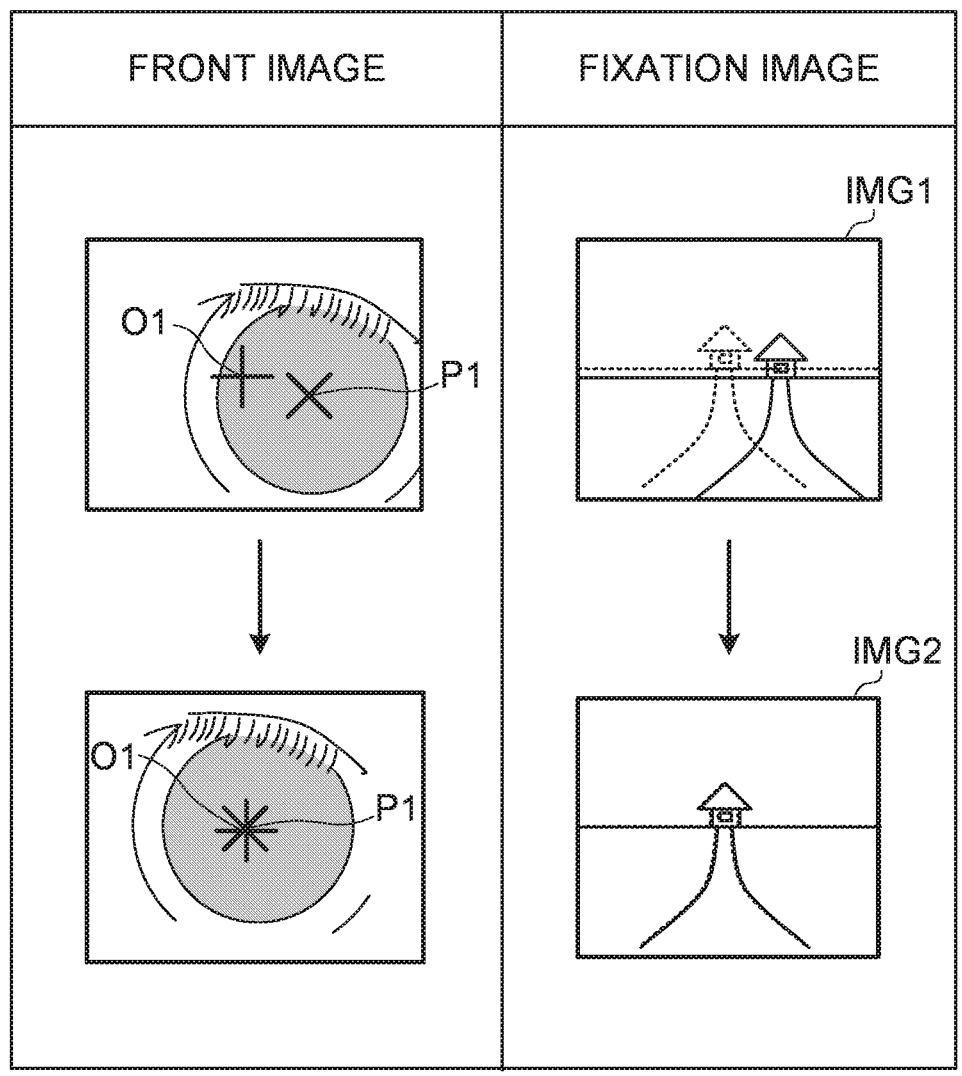
FIG. 10 is a schematic diagram for explaining an operation of the ophthalmologic apparatus according to the embodiments.

FIG. 8 shows a flowchart of an example of the operation of the second alignment operation of the ophthalmologic apparatus 1a according to the second embodiment. FIGS. 9 and 10 show diagrams describing the operation of the ophthalmologic apparatus 1a according to the second embodiment.

Also in the second embodiment, in the second alignment operation in step S3 of FIG. 4, the position matching of the subject's eye E is performed by the subject himself/herself in a state where the movement of the optical system 2a by the movement mechanism 4 is inhibited. At this time, by changing the visual target image depending on the relative position of the subject's eye E with respect to the optical axis O, the subject recognizes the direction and the amount of movement of the subject's eye E to be moved.

(S31) The controller 5a performs control for inhibiting the movement of the optical system 2a by the movement mechanism 4, in the same manner as step S21. The controller 5a can perform control for inhibiting the movement of the optical system 2a by the movement mechanism 4 after controlling the movement mechanism 4 to move the optical system 2a to a reference position.

(S32) Next, the controller 5a determines whether or not the subject's eye E is disposed at a predetermined measurement position, in the same manner as step S22. When it is determined that the subject's eye E is disposed at the predetermined measurement position (S32: Y), the operation of the ophthalmologic apparatus 1a proceeds to step S33. When it is not determined that the subject's eye E is disposed at the predetermined measurement position (S32: N), the ophthalmologic apparatus 1a repeats the process of step S32.

(S33) When it is determined that the subject's eye E is disposed at the predetermined measurement position (S32: Y), the controller 5a controls the fixation optical system 50a to present a fixation target at a predetermined fixation position (for example, a previously defined origin position), in the same manner as step S23.

(S34) Subsequently, the controller 5a causes the illumination optical system 10 to illuminate the anterior segment of the subject's eye E by controlling the illumination optical system 10, and causes the observation optical system 20 to acquire the front image of the anterior segment of the subject's eye E.

(S35) Next, the controller 5a specifies a position of the subject's eye E from the illuminated image of the anterior segment acquired in step S34, and causes the data processor 7a to calculate displacement of the position of the subject's eye E with respect to a predetermined reference position.

(S36) The controller 5a determines whether or not the displacement of the position of the subject's eye obtained in step S35 is equal to or less than a predetermined threshold value, in the same manner as step S26. When it is determined that the displacement is equal to or less than the predetermined threshold value (S36: Y), the second alignment operation terminates (END). When it is determined that the displacement exceeds the predetermined threshold value (S36: N), the operation of the ophthalmologic apparatus 1a proceeds to step S37.

(S37) When it is determined that the displacement exceeds the predetermined threshold value in step S36 (S36: Y), the controller 5a causes the displacement calculator 71a to calculate the displacement between the characteristic site and the position corresponding to the optical axis O in the front image of the subject's eye E acquired by the observation optical system 20. Here, as the position of the characteristic site, a position specified in step S35 may be used. The controller 5a causes the data processor 7a to generate the fixation image depending on the obtained displacement.

The data processor 7a generates, for example, the fixation image. The fixation image is generated by superimposing a reference fixation image IMG0 as shown in FIG. 9 and a displaced fixation image. The displaced fixation image is generated by shifting the reference fixation image IMG0 by the amount of movement corresponding to the calculated displacement in a direction corresponding to the calculated displacement. For example, when the position P1 of the characteristic site (for example, the pupil center region) is shifted from the position O1 corresponding to the optical axis O in the front image of the subject's eye E as shown in FIG. 10, the fixation image IMG1 is generated by superimposing the displaced fixation image, which is shifted depending on the shift amount (displacement), on the reference fixation image IMG0. On the other hand, when the position P1 of the characteristic site substantially coincides with the position O1 corresponding to the optical axis O in the front image of the subject's eye E, the fixation image IMG2 having no shift amount between the reference fixation image and the displaced fixation image is generated.

(S38) The controller 5a causes the liquid crystal display 51a to display the fixation image generated in step S37. Thereby, as the displacement increases, a fixation target having a larger amount of displacement (deviation) between the reference fixation image and the displaced fixation image can be presented to the subject's eye E. When there is no displacement, a fixation target having no displacement between the reference fixation image and the displaced fixation image can be presented to the subject's eye E. Therefore, the subject can recognize the direction and the amount of movement to move the subject's eye E while viewing the fixation target presented by the fixation optical system 50a. And then, the operation of the ophthalmologic apparatus 1a proceeds to step S34.

As described above, in the second embodiment, the subject is made to recognize the direction and the amount of movement of the position of the subject's eye E in the second alignment operation. Thereby, the subject can perform position matching of the subject's eye E with respect to the optical system 2a easily.

Third Embodiment

The ophthalmologic apparatus according to the embodiments may be capable of automatic measurement for both eyes. In this case, the ophthalmologic apparatus can continuously perform measurement on the other subject's eye from one subject's eye of the left subject's eye (left eye) EL and the right subject's eye (right eye) ER in a state where the subject brings his/her face into contact with the holding member 91. Hereinafter, the ophthalmologic apparatus according to the third embodiment will be described mainly about the differences from the first embodiment.

The difference between the configuration of the ophthalmologic apparatus according to the third embodiment and the configuration of the ophthalmologic apparatus 1 according to the first embodiment is mainly the attachment member 90 and movement control contents for the optical system 2 by the movement mechanism 4.

Figure 11:
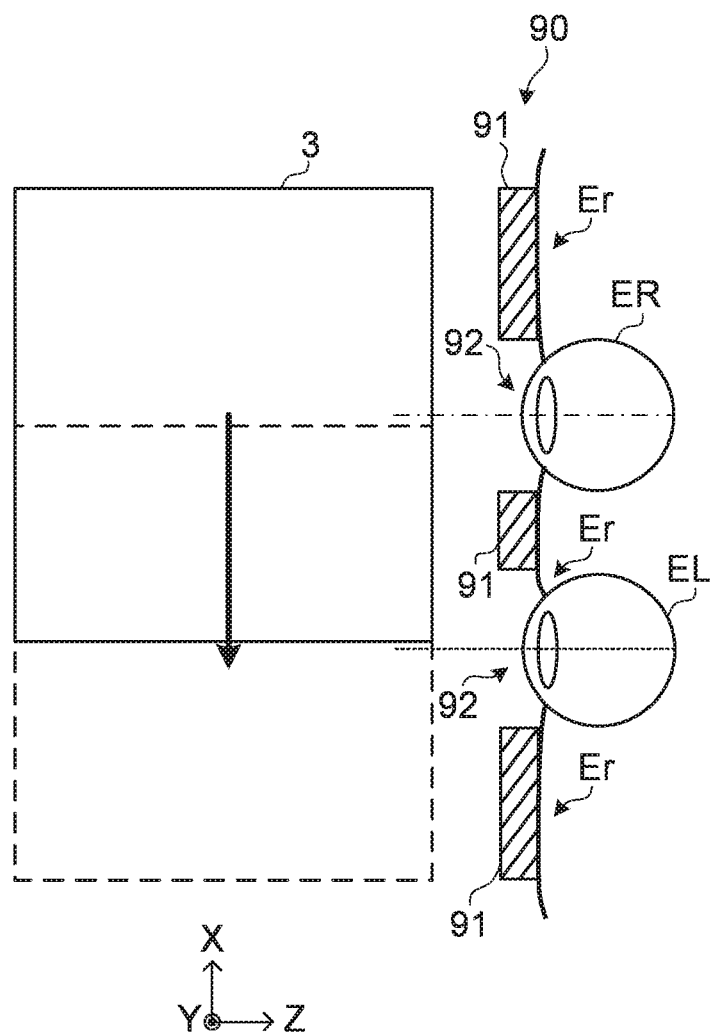
FIG. 11 is a schematic diagram for explaining an operation of the ophthalmologic apparatus according to the embodiments.

FIG. 11 shows a diagram describing the ophthalmologic apparatus according to the third embodiment. In FIG. 11, like reference numerals designate like parts as in FIG. 1. The same description may not be repeated.

In the third embodiment, the passing part 92 is formed in the attachment member 90 so that the optical axis O is capable of passing through for the left subject's eye EL and the right subject's eye ER of the subject. The passing part 92 may be formed at a position corresponding to the left subject's eye EL and the right subject's eye ER. One hole may be formed by combining two holes at positions corresponding to the left subject's eye EL and the right subject's eye ER.

The movement mechanism 4 relatively moves the optical system 2 (housing unit 3) and the attachment member 90 in at least a direction (for example, the X direction) in which the left subject's eye EL and the right subject's eye ER are aligned.

According to the third embodiment, for example, after the measurement of the right subject's eye ER is completed, the subject can continue to measure the left subject's eye EL with the face in contact with the holding member 91.

First Modification Example

In the first to third embodiments, the case has been described in which the front image of the subject's eye E is acquired using the illumination optical system 10 and the observation optical system 20, and the tomographic image of the fundus Ef is acquired by scanning the fundus Ef with the measurement light from the interference optical system 40; however, the configuration of the ophthalmologic apparatus according to the embodiments is not limited thereto.

For example, the interference optical system 40 may be configured to acquire the front image of the anterior segment of the subject's eye E. In this case, for example, an optical element or the like for changing the focal position of the interference optical system 40 to the anterior segment is disposed on the optical axis O between the objective lens (not shown) and the subject's eye E. Hereinafter, the ophthalmologic apparatus according to the first modification example will be described focusing on differences from the first embodiment.

Figure 12:
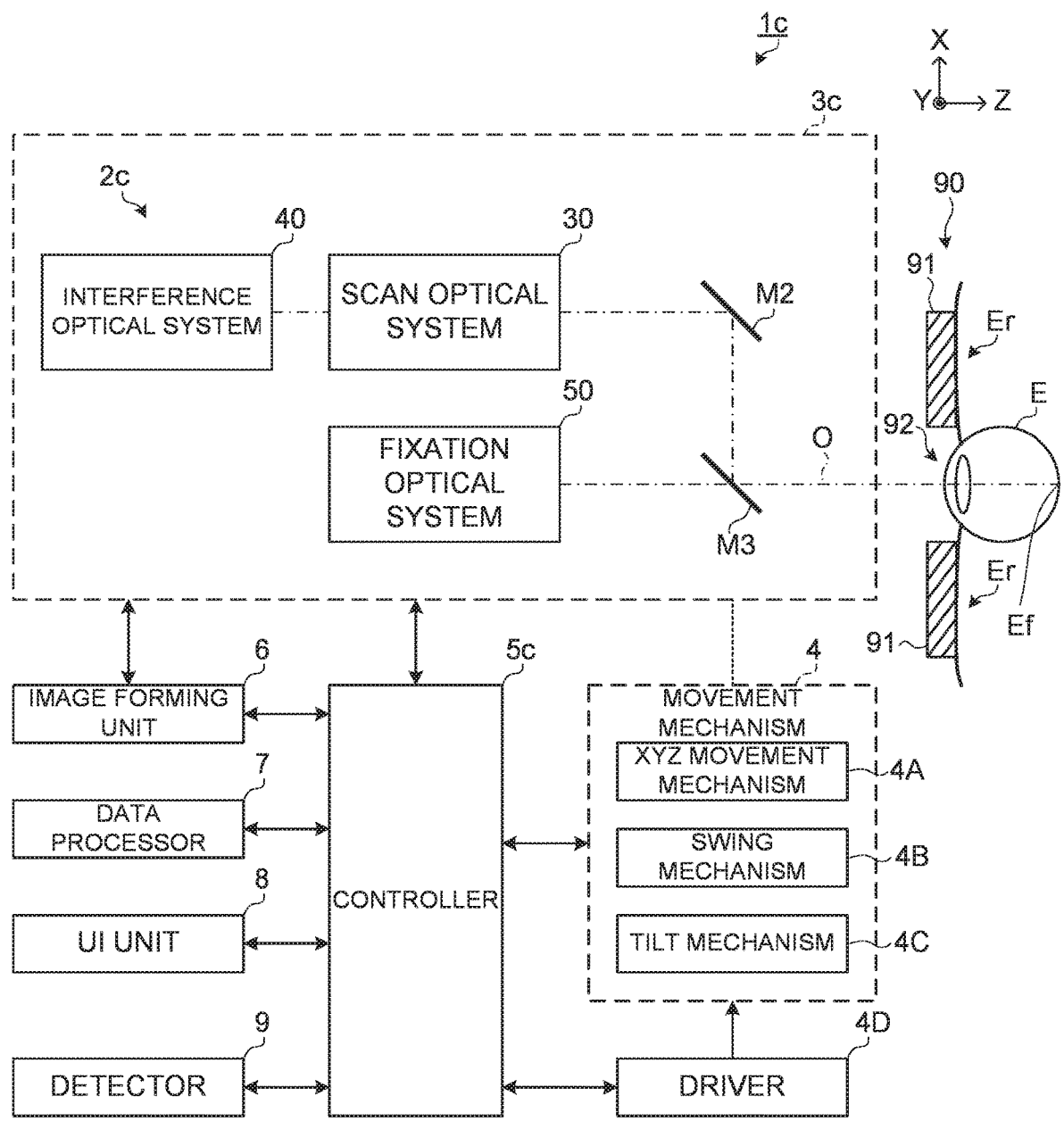
FIG. 12 is a schematic diagram illustrating an example of the configuration of the ophthalmologic apparatus according to a first modification example of the embodiments.

FIG. 12 shows a block diagram of an example of the configuration of the ophthalmologic apparatus according to the first modification example of the embodiments. In FIG. 12, like reference numerals designate like parts as in FIG. 1. The same description may not be repeated.

The difference between the configuration of the ophthalmologic apparatus 1c according to the first modification example and the configuration of the ophthalmologic apparatus 1 according to the first embodiment is mainly that an optical system 2c is provided instead of the optical system 2, and that a controller 5c for controlling corresponding to the optical system 2c is provided instead of the controller 5. The optical system 2c accommodated in the housing unit 3c has a configuration in which the illumination optical system 10, the observation optical system 20, and the beam splitter M1 are omitted from the configuration of the optical system 2. The image forming unit 6 can form the front image and/or the tomographic image of the subject's eye E based on a detection result of the interference light obtained by the interference optical system 40.

According to the first modification example, unintended contact between the subject and the apparatus can be avoided with a simple configuration, even in an ophthalmologic apparatus having a short working distance.

Second Modification Example

In the first to third embodiments, the case has been described in which the scan optical system 30 scans the fundus Ef of the subject's eye E with the measurement light from the interference optical system 40 to acquire the tomographic image of the fundus Ef; however, the configuration of the ophthalmologic apparatus according to the embodiments is not limited thereto. For example, the scan optical system 30 may scan the fundus Ef of the subject's eye E with SLO light from an SLO optical system to acquire the front image of the fundus Ef. Hereinafter, the ophthalmologic apparatus according to the second modification example will be described focusing on differences from the first modification example.

Figure 13:
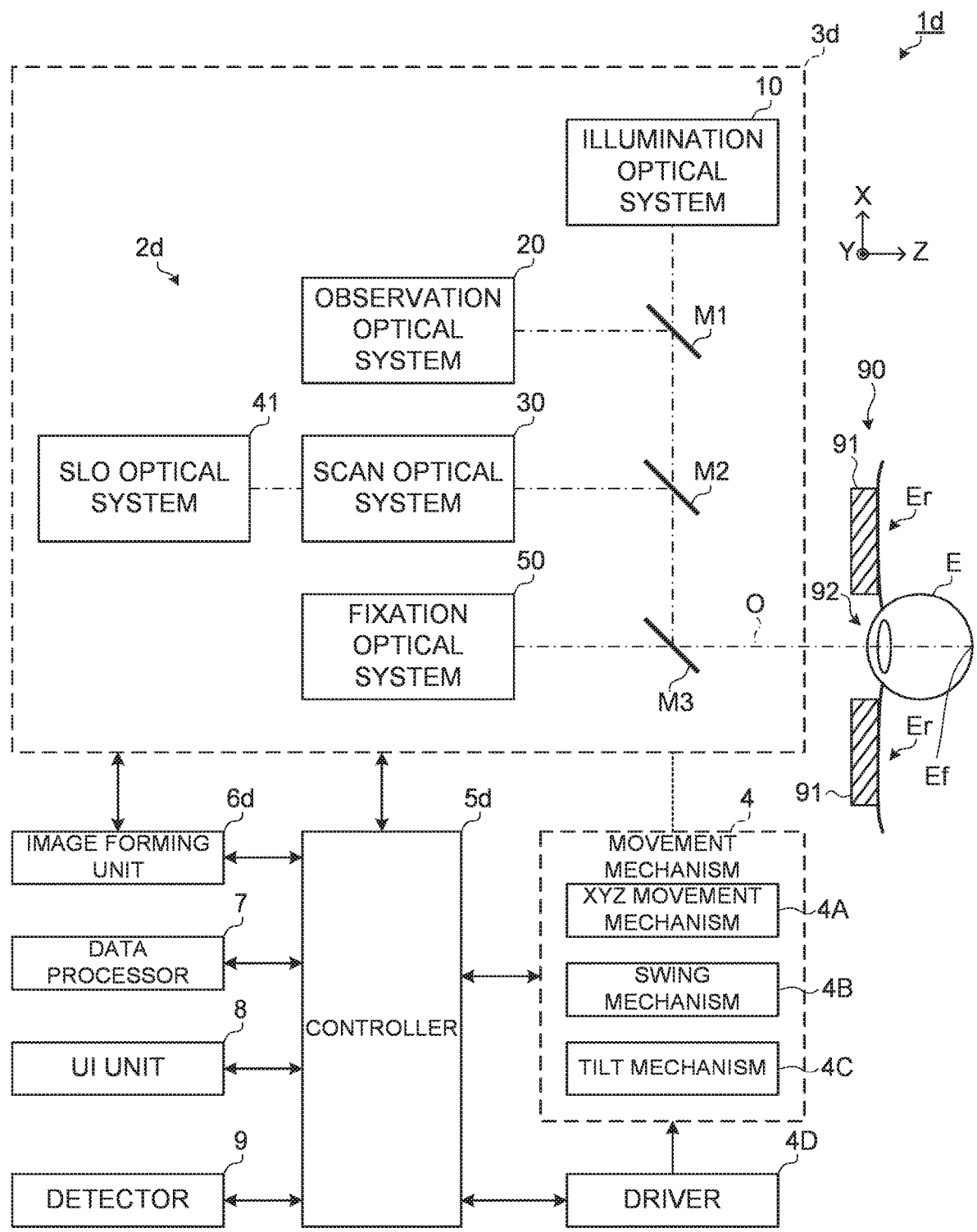
FIG. 13 is a schematic diagram illustrating an example of the configuration of the ophthalmologic apparatus according to a second modification example of the embodiments.

FIG. 13 shows a block diagram of an example of the configuration of the ophthalmologic apparatus according to the second modification example of the embodiments. In FIG. 13, like reference numerals designate like parts as in FIG. 1. The same description may not be repeated.

The difference between the configuration of the ophthalmologic apparatus 1d according to the second modification example and the configuration of the ophthalmologic apparatus 1 according to the first embodiment is mainly that an optical system 2d is provided instead of the optical system 2, that an image forming unit 6d is provided instead of the image forming unit 6, and that a controller 5d for controlling corresponding to the optical system 2d is provided instead of the controller 5. The optical system 2d accommodated in the housing unit 3d has a configuration in which an SLO optical system 41 is provided instead of the interference optical system 40 with respect to the configuration of the optical system 2.

The SLO optical system 41 includes an SLO projection system, an SLO light receiving system, and an optical path coupling member that optically couples the SLO projection system and the SLO light receiving system. The SLO projection system includes an SLO light source, and a lens. The SLO light receiving system includes a lens, a confocal diaphragm, and a detector. The SLO light source includes a laser diode, a super luminescent diode, a laser driven light source, or the like, and outputs light having a wavelength that can be used for SLO. The detector includes, for example, an avalanche photodiode or a photomultiplier tube.

The light beam (SLO light) output from the SLO light source is converted into a parallel light beam (flux) by the lens, is deflected by the scan optical system 30, and is projected onto the fundus Ef through the objective lens. Returning light of the SLO light projected onto the fundus Ef travels through the same path in the opposite direction, and enters the SLO light receiving system. The returning light incident on the SLO light receiving system is collected by the lens, passes through an opening of the confocal diaphragm, and is detected by the detector.

In the optical system 2d as described above, for example, the light output from SLO light source is deflected by the scan optical system 30 and is imaged as spot light on the fundus Ef through the pupil of the subject's eye E. The returning light is light that returns from a projection position (or in the vicinity of the position) of the spot light to the optical system 2d. The returning light is guided to the SLO light receiving system, and is detected by the detector. The detector generates an electrical signal (light reception signal) by photoelectric conversion.

The image forming unit 6d forms a front image (SLO image) of the fundus Ef based on the detection signal (light receiving signal) input from the detector and a pixel position signal input from the controller 5d, for example as is the case with conventional SLO.

The data processor according to the second modification example can form an image of the entire scan area AR by performing position matching of adjacent images on a plurality of images (SLO images) obtained from a plurality of sub-scan areas. At this time, the data processor can perform position matching adjacent images using the overlapping area.

According to the second modification example, unintended contact between the subject and the apparatus can be avoided even in an ophthalmologic apparatus having a short working distance, in the same manner as the first to third embodiments.

Third Modification Example

In the second modification example, the case has been described in which the SLO optical system 41 is provided instead of the interference optical system 40; however, the configuration of the ophthalmologic apparatus according to the embodiments is not limited thereto. For example, both of the interference optical system 40 and the SLO optical system 41 may be provided. Hereinafter, the ophthalmologic apparatus according to the third modification example will be described focusing on differences from the first modification example.

Figure 14:
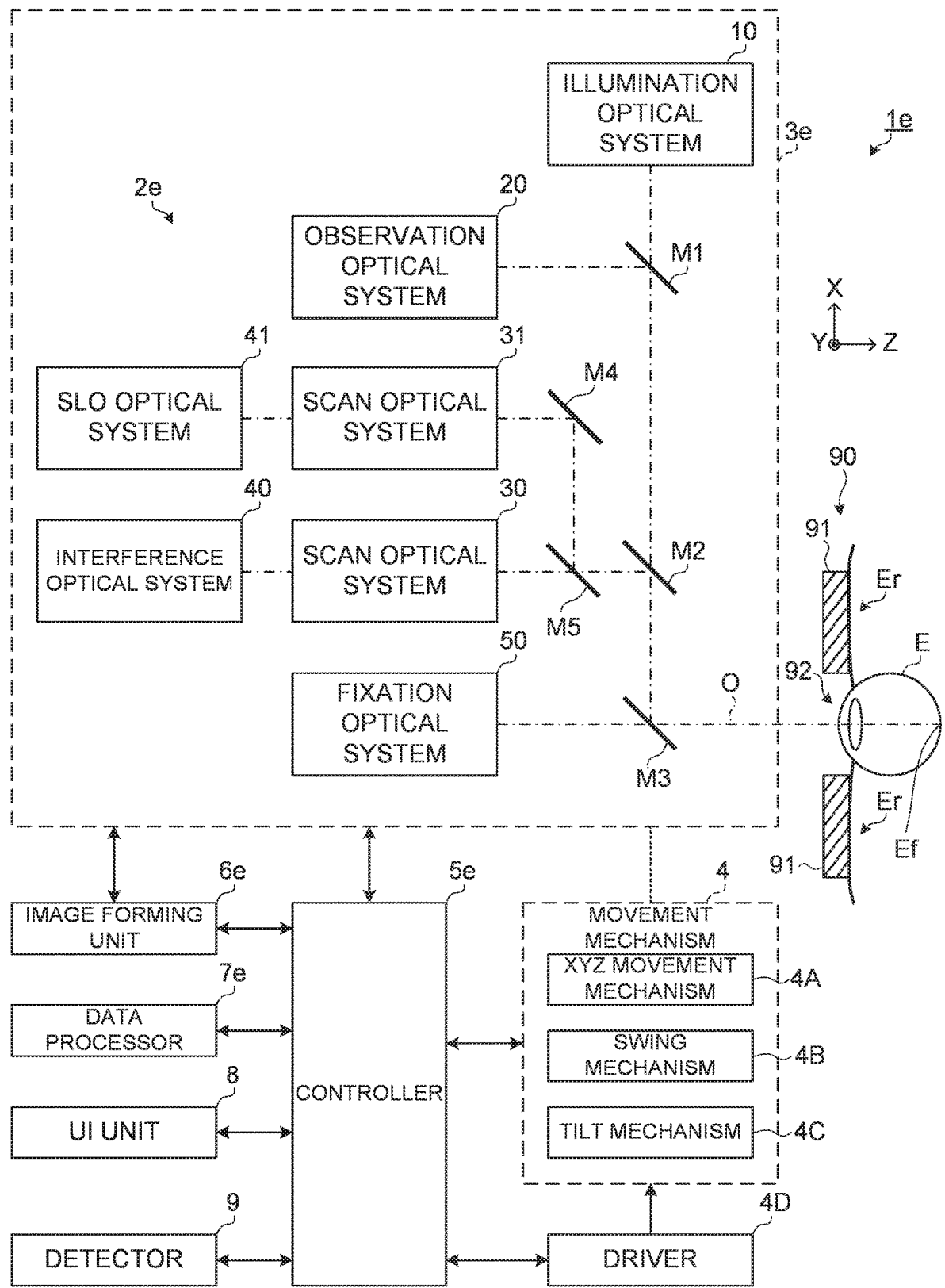
FIG. 14 is a schematic diagram illustrating an example of the configuration of the ophthalmologic apparatus according to a third modification example of the embodiments.

FIG. 14 shows a block diagram of an example of the configuration of the ophthalmologic apparatus according to the third modification example of the embodiments. In FIG. 14, like reference numerals designate like parts as in FIG. 1 or FIG. 13. The same description may not be repeated.

The difference between the configuration of the ophthalmologic apparatus 1e according to the third modification example and the configuration of the ophthalmologic apparatus 1 according to the first embodiment is mainly that an optical system 2e is provided instead of the optical system 2, that an image forming unit 6e is provided instead of the image forming unit 6, that a data processor 7e is provided instead of the data processor 7, and that a controller 5e for controlling corresponding to the optical system 2e is provided instead of the controller 5. The optical system 2e accommodated in the housing unit 3e has a configuration in which an SLO optical system 41, a scan optical system 31, a reflective mirror M4, and a dichroic mirror M5 are added to the configuration of the optical system 2.

The scan optical system 31 has the same configuration as the scan optical system 30. The scan optical system 31 deflects SLO light output from the SLO optical system 41 under the control of the controller 5e. The SLO light deflected by the scan optical system 31 is reflected by the reflective mirror M4, is reflected by the dichroic mirror M5, and is reflected toward the subject's eye E by the beam splitters M2 and M3. Thereby, the spot position on the fundus Ef is moved. Returning light of the SLO light from the fundus Ef travels through the same path in the opposite direction, and is detected in the SLO light receiving system of the SLO optical system 41.

The image forming unit 6e forms a tomographic image and/or a front image of the fundus Ef based on the detection signal (light receiving signal) input from the detector and a pixel position signal input from the controller 5*e*, for example as is the case with conventional OCT. In addition, the image forming unit 6*e* forms a front image (SLO image) of the fundus Ef based on the detection signal (light receiving signal) input from the detector and a pixel position signal input from the controller 5*e*, for example as is the case with conventional SLO.

The data processor 7*e* can form an image of the entire scan area AR by performing position matching of adjacent images on a plurality of images (OCT images, SLO images) obtained from a plurality of sub-scan areas. At this time, the data processor 7*e* can perform position matching adjacent images using the overlapping area.

According to the third modification example, unintended contact between the subject and the apparatus can be avoided even in an ophthalmologic apparatus having a short working distance, in the same manner as the first to third embodiments.

<Effects>

The effects of the ophthalmologic apparatus according to the embodiments are explained.

An ophthalmologic apparatus (1, 1*a*, 1*c*, 1*d*, 1*e*) according to the embodiments includes an optical system (2, 2*a*, 2*c*, 2*d*, 2*e*), a housing unit (3, 3*a*, 3*c*, 3*d*, 3*e*), and an attachment member (90). The optical system is used for acquiring data of a subject's eye (E). The housing unit is configured to house (accommodate) the optical system. The attachment member includes a holding member (91), and is configured to be detachable between the housing unit and the subject's eye. The holding member is configured to hold a face of the subject movably in a state where a peripheral site of the subject's eye is in contact with the holding member. A passing part (92) through which an optical axis of the optical system passes is formed in the holding member.

According to such a configuration, the attachment member is configured to attach between the housing unit for housing the optical system and the subject's eye. Thereby, the ophthalmologic apparatus capable of changing the position of the subject's eye with respect to the optical system by the movement of the subject himself/herself can be provided. When the data of the subject's eye is acquired over a wide range, the working distance is shortened. However, even in such a case, the subject himself/herself can finely adjust the position of the subject's eye. Thereby, unintended contact between the apparatus (for example, the optical system or the housing unit) and the subject (for example, a part of the face or the subject's eye) can be avoided.

Further, in the ophthalmologic apparatus according to the embodiments, the holding member may have elasticity in at least one direction of a direction of the optical axis (Z direction) of the optical system and a direction intersecting the direction(s) of the optical axis (X direction, Y direction) at least in a part where the peripheral site is contacted.

According to such a configuration, by changing the position of the subject's eye in at least one of the direction of the optical axis of the optical system and the direction(s) intersecting the direction of the optical axis, the ophthalmologic apparatus capable of avoiding unintended contact between the apparatus and the subject by the movement of the subject himself/herself can be provided.

Further, in the ophthalmologic apparatus according to the embodiments, the holding member may have a thickness in the direction of the optical axis such that the subject's eye is disposed at a position corresponding to a working distance of the optical system when the peripheral site is in contact with the holding member.

According to such a configuration, even when the subject moves excessively, it becomes possible to prevent the optical system from approaching the predetermined subject's eye position corresponding to the working distance. Thereby, the possibility of contact between the subject and the apparatus can be further reduced.

Further, the ophthalmologic apparatus according to the embodiments may further include a movement mechanism (4), a driver (4D), a detector (9), and a controller (5, 5*a*, 5*c*, 5*d*, 5*e*). The movement mechanism is configured to move the optical system. The driver is configured to drive the movement mechanism. The detector is configured to detect whether or not the attachment member is attached to the ophthalmologic apparatus. The controller is configured to control the driver based on a detection result obtained by the detector.

According to such a configuration, the movement of the optical system is controlled depending on the detection result of the attachment state of the attachment member. Thereby, an ophthalmologic apparatus, that automatically shifts so that the position of the subject's eye can be changed with respect to the optical system by the movement of the subject when the attachment member is attached, can be provided.

Further, in the ophthalmologic apparatus according to the embodiments, the controller may be configured to inhibit movement of the optical system by the movement mechanism when it is detected by the detector that the attachment member is attached to the ophthalmologic apparatus.

According to such a configuration, the position of the optical system is fixed when the position of the subject's eye with respect to the optical system is changed by the movement of the subject. Thereby, while avoiding unintended contact between the subject and the apparatus, the position of the subject's eye with respect to the optical system by the subject himself/herself can be adjusted easily.

Further, in the ophthalmologic apparatus according to the embodiments, the controller may be configured to perform a first alignment operation when it is detected by the detector that the attachment member is not attached, and to perform a second alignment operation when it is detected by the detector that the attachment member is attached.

According to such a configuration, the alignment operation is changed depending on the detection result of the attachment state of the attachment member. Thereby, the following ophthalmologic apparatus can be provided. In this ophthalmologic apparatus, when the attachment member is attached, the position of the subject's eye with respect to the optical system can be changed by the movement of the subject. And, in this ophthalmologic apparatus, when the attachment member is not attached, operation mode is automatically shifted to perform another alignment operation.

Further, in the ophthalmologic apparatus according to the embodiment, the optical system may include an interference optical system (40) configured to split light from a light source into reference light and measurement light, to project the measurement light onto the subject's eye, and to detect interference light between returning light of the measurement light from the subject's eye and the reference light; and an observation optical system (20) for observing the subject's eye. The controller may be configured to control movement of the optical system in a direction of the optical axis based on detection result of the interference light obtained by the interference optical system, and to control the movement of the optical system in a direction intersecting the direction of the optical axis based on a position of a characteristic site in a front image of the subject's eye obtained by the observation optical system, as the first alignment operation.

According to such a configuration, the position of the subject's eye with respect to the optical system can be changed by the movement of the subject himself/herself when the attachment member is attached. Thereby, an ophthalmologic apparatus, that can automatically perform position matching of the subject's eye with respect to the optical system based on an image obtained by the interference optical system or the observation optical system when the attachment member is not attached, can be provided.

Further, ophthalmologic apparatus according to the embodiments further may include an image forming unit (6, 6d, 6e) configured to form a tomographic image of the subject's eye based on a detection result of the interference light obtained by the interference optical system.

According to such a configuration, the interference optical system for acquiring a tomographic image of the subject's eye can be used for the first alignment operation. Thereby, the ophthalmologic apparatus can be downsized.

Further, in the ophthalmologic apparatus according to the embodiment, the optical system may include an interference optical system (40) configured to split light from the optical system into measurement light and reference light, to project the measurement light onto the subject's eye, and to detect interference light between returning light of the measurement light from the subject's eye and the reference light. The controller may be configured to control movement of the optical system in a direction of the optical axis and a direction intersecting the direction of the optical system based on detection result of the interference light obtained by the interference optical system, as the first alignment operation.

According to such a configuration, the position of the subject's eye with respect to the optical system can be changed by the movement of the subject himself/herself when the attachment member is attached. Thereby, an ophthalmologic apparatus, that can automatically perform position matching of the subject's eye with respect to the optical system based on an image obtained by the interference optical system when the attachment member is not attached, can be provided.

Further, the ophthalmologic apparatus according to the embodiments further may include an image forming unit (6, 6d, 6e) configured to form a tomographic image and a front image of the subject's eye based on a detection result of the interference light obtained by the interference optical system.

According to such a configuration, the interference optical system for acquiring a tomographic image of the subject's eye can be used for the first alignment operation. Thereby, the ophthalmologic apparatus can be downsized.

Further, in the ophthalmologic apparatus according to the embodiments, the optical system may include a fixation optical system (50, 50a) configured to project a fixation light flux onto the subject's eye, and the controller may be configured to control the fixation optical system so as to present a fixation target at a predetermined fixation position, as the second alignment operation.

According to such a configuration, the fixation target is presented at the predetermined fixation position when the attachment member is attached. Thereby, the position of the pupil of the subject's eye is fixed, and it becomes easy to change the position of the subject's eye by the movement of the subject alone.

Further, in the ophthalmologic apparatus according to the embodiments, the optical system may include a fixation optical system (50a) configured to project a fixation target onto the subject's eye, and the controller may be configured to specify a relative position of the subject's eye with respect to the optical system based on the front image of the subject's eye, and to control the fixation optical system depending on the specified relative position.

According to such a configuration, the fixation target presented to the subject's eye is controlled depending on the relative position of the subject's eye with respect to the optical system, when the attachment member is attached. Thereby, the subject can be made to recognize the direction and the amount of movement of the subject's eye to be moved.

Further, in the ophthalmologic apparatus according to the embodiments, the passing part may be formed so that the optical axis is capable of passing through for a left eye (left subject's eye EL) and a right eye (right subject's eye ER) of the subject, and the movement mechanism may be configured to move the optical system and the attachment member in at least a direction in which the left eye and the right eye are aligned.

According to such a configuration, while bringing the face of the subject into contact with the holding member, after the measurement of one of the left eye and the right eye is completed, the measurement of the other eye can be continued.

The above-described embodiments are merely examples for carrying out the present invention. Those who intend to implement the present invention can apply any modification, omission, addition, or the like within the scope of the gist of the present invention.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An ophthalmologic apparatus, comprising:
an optical system configured to acquire data of a subject's eye;
a housing unit configured to house the optical system;
an attachment member including a holding member configured to hold a face of the subject movably in a state where a peripheral site of the subject's eye is in contact with the holding member, a passing part through which an optical axis of the optical system passes being formed in the holding member, and the attachment member configured to be detachable between the housing unit and the subject's eye;

a movement mechanism configured to move the optical system;

a driver configured to driver the movement mechanism;

a detector configured to detect whether or not the attachment member is attached to the ophthalmologic apparatus; and a controller configured to control the driver based on a detection result obtained by the detector, wherein the controller is configured to perform a first alignment operation when it is detected by the detector that the attachment member is not attached, and to perform a second alignment operation when it is detected by the detector that the attachment member is attached.

2. The ophthalmologic apparatus of claim 1, wherein the holding member has elasticity in at least one direction of a direction of the optical axis of the optical system and a direction intersecting the direction of the optical axis at least in a part where the peripheral site is contacted.

3. The ophthalmologic apparatus of claim 1, wherein the holding member has a thickness in the direction of the optical axis such that the subject's eye is disposed at a position corresponding to a working distance of the optical system when the peripheral site is in contact with the holding member.

4. The ophthalmologic apparatus of claim 1, wherein the controller is configured to inhibit movement of the optical system by the movement mechanism when it is detected by the detector that the attachment member is attached to the ophthalmologic apparatus.

5. The ophthalmologic apparatus of claim 1, wherein the optical system comprises:

an interference optical system configured to split light from a light source into reference light and measurement light, to project the measurement light onto the subject's eye, and to detect interference light between returning light of the measurement light from the subject's eye and the reference light; and an observation optical system for observing the subject's eye, wherein the controller is configured to control movement of the optical system in a direction of the optical axis based on detection result of the interference light obtained by the interference optical system, and to control the movement of the optical system in a direction intersecting the direction of the optical axis based on a position of a characteristic site in a front image of the subject's eye obtained by the observation optical system, as the first alignment operation.

6. The ophthalmologic apparatus of claim 5, further comprising:

an image forming unit configured to form a tomographic image of the subject's eye based on a detection result of the interference light obtained by the interference optical system.

7. The ophthalmologic apparatus of claim 5, wherein the optical system includes a fixation optical system configured to present a fixation target to the subject's eye, and the controller is configured to specify a relative position of the subject's eye with respect to the optical system based on the front image of the subject's eye, and to control the fixation optical system depending on the specified relative position.

8. The ophthalmologic apparatus of claim 1, wherein the optical system includes an interference optical system configured to split light from the optical system is configured into measurement light and reference light, to project the measurement light onto the subject's eye, and to detect interference light between returning light of the measurement light from the subject's eye and the reference light, and the controller is configured to control movement of the optical system in a direction of the optical axis and a direction intersecting the direction of the optical system based on detection result of the interference light obtained by the interference optical system, as the first alignment operation.

9. The ophthalmologic apparatus of claim 8, further comprising:

an image forming unit configured to form a tomographic image and a front image of the subject's eye based on a detection result of the interference light obtained by the interference optical system.

10. The ophthalmologic apparatus of claim 9, wherein the optical system includes a fixation optical system configured to present a fixation target to the subject's eye, and the controller is configured to specify a relative position of the subject's eye with respect to the optical system based on the front image of the subject's eye, and to control the fixation optical system depending on the specified relative position.

11. The ophthalmologic apparatus of claim 1, wherein the optical system includes a fixation optical system configured to project a fixation light flux onto the subject's eye, and the controller is configured to control the fixation optical system so as to present a fixation target at a predetermined fixation position, as the second alignment operation.

12. The ophthalmologic apparatus of claim 1, wherein the passing part is formed so that the optical axis is capable of passing through for a left eye and a right eye of the subject, and the movement mechanism is configured to relatively move the optical system and the attachment member in at least a direction in which the left eye and the right eye are aligned.

* * * * *